US008765926B2

(12) United States Patent
Pompon et al.

(10) Patent No.: US 8,765,926 B2
(45) Date of Patent: Jul. 1, 2014

(54) MULTIDIMENSIONAL SUPRAMOLECULAR STRUCTURES ESSENTIALLY MADE OF ASSEMBLED I-MOTIF TETRAMERS

(71) Applicant: Centre National de la Recherche Scientifique, Paris (FR)

(72) Inventors: Denis Pompon, Gif-sur-Yvette (FR); Jean-Louis Leroy, Antony (FR); Aude Laisne, Gif-sur-Yvette (FR)

(73) Assignee: Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 13/716,851

(22) Filed: Dec. 17, 2012

(65) Prior Publication Data

US 2013/0109848 A1    May 2, 2013

Related U.S. Application Data

(63) Continuation of application No. 13/504,772, filed as application No. PCT/IB2010/002977 on Oct. 28, 2010, now abandoned.

(30) Foreign Application Priority Data

Oct. 29, 2009    (EP) .................................... 09290826

(51) Int. Cl.
*C07H 1/00*    (2006.01)
*C07H 21/04*    (2006.01)

(52) U.S. Cl.
USPC ........................ 536/23.1; 536/24.2

(58) Field of Classification Search
USPC .............................. 536/23.1, 24.2
See application file for complete search history.

(56) References Cited

U.S. PATENT DOCUMENTS 5,625,051 A * 4/1997 Gehring et al. .............. 536/24.2

OTHER PUBLICATIONS

Mergny et al. J. Am. Chem. Soc., vol. 117, No. 35, 8887-8898, 1995.*
Zhao, A DNA Nanomachine Induced by Single-Walled Carbon Nanotubes on Gold Surface, Biomaterials, 30, pp. 1739-1745, 2009.
Leroy, T.T Pair Intercalation and Duplex Interconversion Within i-Motif Tetramers, Journal of Molecular Biology, 333, pp. 125-139, 2003.
Leroy, The Formation Pathway of i-Motif Tetramers, Nucleic Acids Research, 37, pp. 4127-4134, 2009.
Mergny, Intramolecular Folding of Pyrimidine Oligodeoxynucleotides into an i-DNA Motif, Journal of the American Chemical Society, 117, pp. 8887-8898, 1995.
Seela, pH-Dependent Assembly of DNA-Gold Nanoparticles Based on the i-Motif: A Switchable Device with the Potential of a Nanomachine, Helvetica Chimica Acta, 89, pp. 1978-1985, 2006.
Ghodke, The I-Tetraplex Building Block: Rational Design and Controlled Fabrication of Robust 1D DNA Scaffolds Through Non-Watson-Crick Interactions, Angewandte Chemie, 46, pp. 2646-2649, 2007.
Laisne, [C1GC4]4 Association into Supra Molecular i-Motif Structures, Nucleic Acids Research, 38, pp. 3817-3826, 2010.

* cited by examiner

*Primary Examiner* — Janet Epps-Smith
(74) *Attorney, Agent, or Firm* — Morgan, Lewis & Bockius LLP

(57) ABSTRACT

The present invention pertains to a supramolecular structure based on i-motif tetramers of $C_m$—X—$C_n$ oligonucleotides, wherein m and n are integers comprised between 2 and 9, and X is a linker such as A, T, G, a modified deoxynucleotide or a diol spacer. These supramolecular structures can be dissociated, when necessary, by a mere pH change. The present invention also relates to methods for obtaining such a supramolecular structure.

26 Claims, 14 Drawing Sheets

Figure 1:
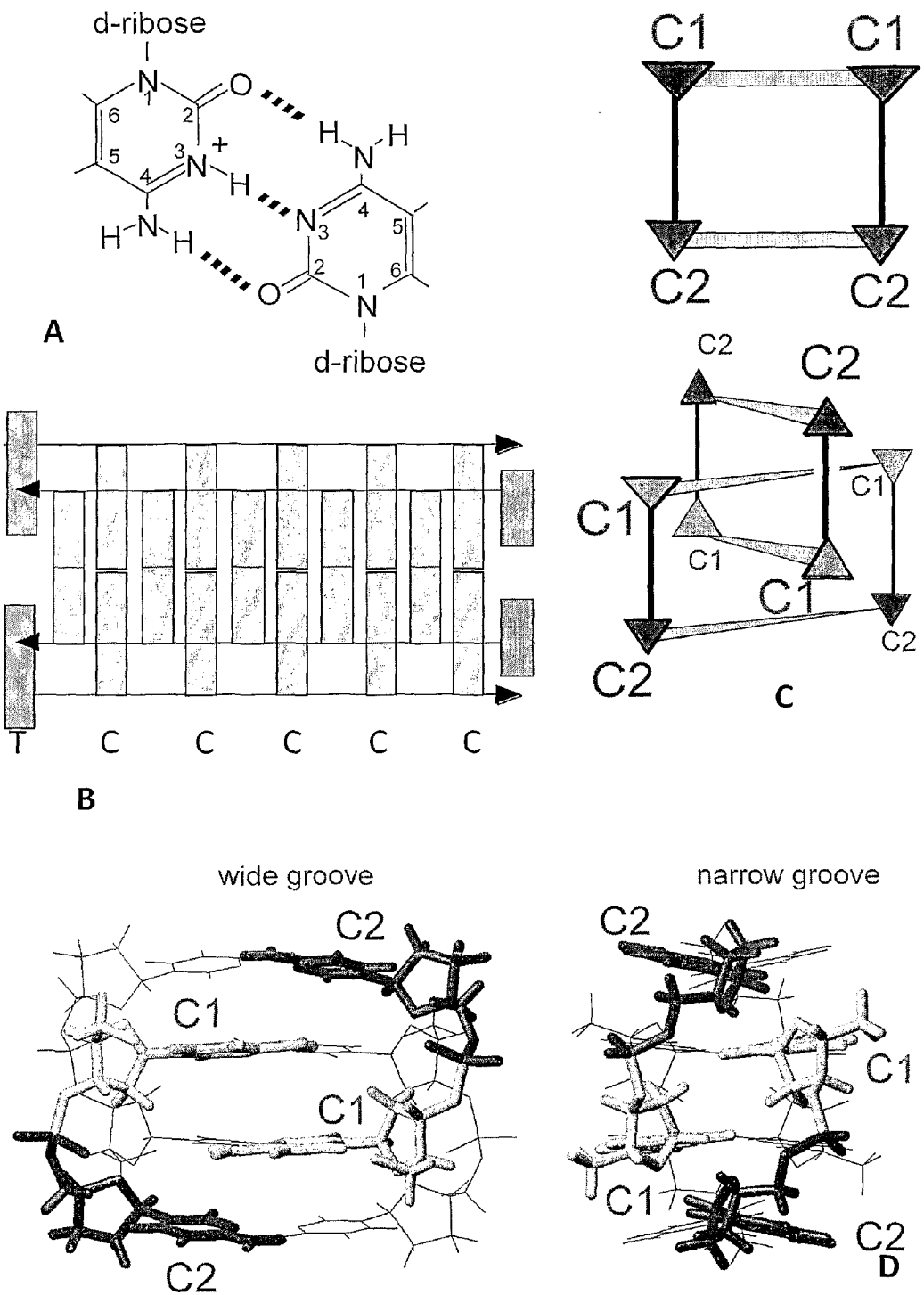

```
                         SEQUENCE LISTING

<160> NUMBER OF SEQ ID NOS: 24

<210> SEQ ID NO 1
<211> LENGTH: 5
<212> TYPE: DNA
<213> ORGANISM: artificial
<220> FEATURE:
<223> OTHER INFORMATION: oligonucleotide
<220> FEATURE:
<221> NAME/KEY: misc_feature
<222> LOCATION: (2)..(2)
<223> OTHER INFORMATION: can be replaced by 2 to 8 cytosine residues
<220> FEATURE:
<221> NAME/KEY: misc_feature
<222> LOCATION: (3)..(3)
<223> OTHER INFORMATION: can be replaced by one to 3 ribo- or deoxyribo-
      A, T, G or U nucleotides, modified ribo or deoxyribonucletides, or
      diol spacer
<220> FEATURE:
<221> NAME/KEY: misc_feature
<222> LOCATION: (4)..(4)
<223> OTHER INFORMATION: can be replaced by 2 to 8 cytosine residues

<400> SEQUENCE: 1 ccdcc                                                              5

<210> SEQ ID NO 2
<211> LENGTH: 12
<212> TYPE: DNA
<213> ORGANISM: Artificial
<220> FEATURE:
<223> OTHER INFORMATION: oligonucleotide

<400> SEQUENCE: 2 ccccccgcc cc                                                      12

<210> SEQ ID NO 3
<211> LENGTH: 12
<212> TYPE: DNA
<213> ORGANISM: Artificial
<220> FEATURE:
<223> OTHER INFORMATION: oligonucleotide

<400> SEQUENCE: 3
ccccgccccc cc                                                     12

<210> SEQ ID NO 4
<211> LENGTH: 12
<212> TYPE: DNA
<213> ORGANISM: Artificial
<220> FEATURE:
<223> OTHER INFORMATION: oligonucleotide

<400> SEQUENCE: 4 cccccctcc cc                                                      12

<210> SEQ ID NO 5
<211> LENGTH: 12
<212> TYPE: DNA
<213> ORGANISM: Artificial
<220> FEATURE:
<223> OTHER INFORMATION: oligonucleotide

<400> SEQUENCE: 5
cccctccccc cc                                                     12
```

```
<210> SEQ ID NO 6
<211> LENGTH: 5
<212> TYPE: DNA
<213> ORGANISM: Artificial
<220> FEATURE:
<223> OTHER INFORMATION: terminator oligonucleotide
<220> FEATURE:
<221> NAME/KEY: misc_feature
<222> LOCATION: (3)..(3)
<223> OTHER INFORMATION: can be replaced by 2 to 6 cytosine residues
<220> FEATURE:
<221> NAME/KEY: misc_feature
<222> LOCATION: (4)..(4)
<223> OTHER INFORMATION: can be replaced by U, a modified ribo or
      deoxyribonucleotide, or diol spacer
<220> FEATURE:
<221> NAME/KEY: misc_feature
<222> LOCATION: (5)..(5)
<223> OTHER INFORMATION: can be replaced by nothing or by one to 9 ribo-
      or deoxyribo- A, T, C, G or U nucleotides, possibly modified, with
      the provisio that no cytosine residue is followed by another
      cytosine residue

<400> SEQUENCE: 6 cccdd                                                                       5

<210> SEQ ID NO 7
<211> LENGTH: 5
<212> TYPE: DNA
<213> ORGANISM: Artificial
<220> FEATURE:
<223> OTHER INFORMATION: oligonucleotide

<400> SEQUENCE: 7 tcccc                                                                       5

<210> SEQ ID NO 8
<211> LENGTH: 6
<212> TYPE: DNA
<213> ORGANISM: Artificial
<220> FEATURE:
<223> OTHER INFORMATION: oligonucleotide

<400> SEQUENCE: 8 tccccc                                                                      6

<210> SEQ ID NO 9
<211> LENGTH: 12
<212> TYPE: DNA
<213> ORGANISM: Artificial
<220> FEATURE:
<223> OTHER INFORMATION: oligonucleotide
<220> FEATURE:
<221> NAME/KEY: misc_feature
<222> LOCATION: (8)..(8)
<223> OTHER INFORMATION: can be replaced by A, T, G, U, a modified ribo
      or deoxyribonucleotide, or a diol spacer

<400> SEQUENCE: 9
cccccccdcc cc                                                              12

<210> SEQ ID NO 10
<211> LENGTH: 8
<212> TYPE: DNA
<213> ORGANISM: Artificial
<220> FEATURE:
<223> OTHER INFORMATION: oligonucleotide

<400> SEQUENCE: 10
``` cccccct                                                                                  8

<210> SEQ ID NO 11
<211> LENGTH: 10
<212> TYPE: DNA
<213> ORGANISM: Artificial
<220> FEATURE:
<223> OTHER INFORMATION: oligonucleotide

<400> SEQUENCE: 11
cccccctccc                                                                               10

<210> SEQ ID NO 12
<211> LENGTH: 11
<212> TYPE: DNA
<213> ORGANISM: Artificial
<220> FEATURE:
<223> OTHER INFORMATION: oligonucleotide

<400> SEQUENCE: 12
ccccccctcc c                                                                             11

<210> SEQ ID NO 13
<211> LENGTH: 11
<212> TYPE: DNA
<213> ORGANISM: Artificial
<220> FEATURE:
<223> OTHER INFORMATION: oligonucleotide

<400> SEQUENCE: 13
cccccctccc c                                                                             11

<210> SEQ ID NO 14
<211> LENGTH: 14
<212> TYPE: DNA
<213> ORGANISM: Artificial
<220> FEATURE:
<223> OTHER INFORMATION: oligonucleotide

<400> SEQUENCE: 14 ccccccctc cccc                                                                           14

<210> SEQ ID NO 15
<211> LENGTH: 12
<212> TYPE: DNA
<213> ORGANISM: Artificial
<220> FEATURE:
<223> OTHER INFORMATION: oligonucleotide

<400> SEQUENCE: 15
ttcccccccc tt                                                                            12

<210> SEQ ID NO 16
<211> LENGTH: 9
<212> TYPE: DNA
<213> ORGANISM: Artificial
<220> FEATURE:
<223> OTHER INFORMATION: oligonucleotide

<400> SEQUENCE: 16 cccctcccc                                                                                9

<210> SEQ ID NO 17
<211> LENGTH: 7
<212> TYPE: DNA
<213> ORGANISM: Artificial

```
<220> FEATURE:
<223> OTHER INFORMATION: oligonucleotide

<400> SEQUENCE: 17 cctctcc                                                                    7

<210> SEQ ID NO 18
<211> LENGTH: 9
<212> TYPE: DNA
<213> ORGANISM: Artificial
<220> FEATURE:
<223> OTHER INFORMATION: oligonucleotide
<220> FEATURE:
<221> NAME/KEY: misc_feature
<222> LOCATION: (3)..(3)
<223> OTHER INFORMATION: can be replace by 1 to 8 cytosine residue(s)

<400> SEQUENCE: 18 cctctctcc                                                                  9

<210> SEQ ID NO 19
<211> LENGTH: 4
<212> TYPE: DNA
<213> ORGANISM: Artificial
<220> FEATURE:
<223> OTHER INFORMATION: oligonucleotide

<400> SEQUENCE: 19 tccc                                                                       4

<210> SEQ ID NO 20
<211> LENGTH: 3
<212> TYPE: DNA
<213> ORGANISM: Artificial
<220> FEATURE:
<223> OTHER INFORMATION: oligonucleotide
<220> FEATURE:
<221> NAME/KEY: misc_feature
<222> LOCATION: (3)..(3)
<223> OTHER INFORMATION: can be replaced by 2 to 8 cytosine residues

<400> SEQUENCE: 20 tcc                                                                        3

<210> SEQ ID NO 21
<211> LENGTH: 7
<212> TYPE: DNA
<213> ORGANISM: Artificial
<220> FEATURE:
<223> OTHER INFORMATION: oligonucleotide

<400> SEQUENCE: 21 ccccccc                                                                    7

<210> SEQ ID NO 22
<211> LENGTH: 8
<212> TYPE: DNA
<213> ORGANISM: Artificial
<220> FEATURE:
<223> OTHER INFORMATION: oligonucleotide

<400> SEQUENCE: 22 ccccctcc                                                                   8

<210> SEQ ID NO 23
<211> LENGTH: 8
<212> TYPE: DNA
```

```
<213> ORGANISM: Artificial
<220> FEATURE:
<223> OTHER INFORMATION: oligonucleotide

<400> SEQUENCE: 23 cctcccc                                                                 8

<210> SEQ ID NO 24
<211> LENGTH: 7
<212> TYPE: DNA
<213> ORGANISM: Artificial
<220> FEATURE:
<223> OTHER INFORMATION: oligonucleotide

<400> SEQUENCE: 24 ccctccc                                                                 7
```

MULTIDIMENSIONAL SUPRAMOLECULAR STRUCTURES ESSENTIALLY MADE OF ASSEMBLED I-MOTIF TETRAMERS

The present invention concerns the field of nanotechnology. More precisely, the present invention relates to nanostructures obtained by self-assembly of molecules. The invention is indeed based on the demonstration that oligonucleotides of specific sequences can be used to obtain tuneable supramolecular structures which can be dissociated, when necessary, by a mere pH change.

A rather large number of bio-assisted or bio-mimetic strategies based on the self-assembly properties of biological building blocks like proteins or nucleic acids have been proposed in recent literature for construction of nano-devices.

In particular, double-stranded DNA has been used for obtaining self-assembled structures, such as in the ORIGAMI approach (Rothemund, 2006). The use of DNA as a nanoscale scaffold has also attracted much attention for the construction of objects such as templated nanowires (Yan et al., 2003), self-assembling 2D and 3D arrays (Park et al., 2006) and molecular machines (Chen and Mao, 2004). The exceptional utility of DNA for this purpose is determined by its capacity to act both in specific recognition and as a structural element. Moreover, the ease of synthesis, modification and manipulation of DNA enhances its attractiveness as a building block for nanostructures. Self-assembly most of time involves classical DNA base-paring and associates various combination of DNA-B double-stranded segments spatially linked and organized either through strand exchange or/and two or three-way junctions (Holiday junction types) (Paukstelis et al., 2004).

However, practical interest of the current approaches remains limited due to three major bottlenecks:

(i) Most of current bio-assisted self-assembly strategies involve a single type a biomaterial at a time, mostly of peptidic or nucleic acid nature which both have some advantages and limitations, whereas practical use would require association of several types of material into an integrated approach.

(ii) Self-assembly of biomaterial is extremely sensitive to kinetic trapping, an effect that results in high proportion of long-lived defective structures and slow formation of the thermodynamically stable species. Thermal cycling of nucleic acid-based self-assemblies reduces the proportion of defective structures and favors the well-defined programmed nucleic acid supramolecular assembly. However, this thermal approach is catastrophic when peptidic/protein components are involved in the structure.

(iii) Self-assembly of bio-structures is generally performed in a 3D-(solution) environment, although most of current applications require 2D-(surface) controlled organization. Transfer of preformed complex structures from a 3D- to a 2D-environment almost always lead to a high rate of defects associated with the dimensional reduction.

Recently, 1-dimensional supramolecular structures based on i-motif DNA tetramers have been described (Ghodke et al., 2007). These structures, called I-wires, have been obtained by using poly-cytosine polymers ($d(C_7)$ and $d(C_9)$). Ghodke et al. however did not describe 2-D or 3-D structures.

The i-motif structure, first described by Gehring, Leroy and Guéron, is exceptional in that it involves systematic base-pair intercalation (Gehring et al., 1993). At slightly acid pH, the hemiprotonated C·C+ pairs formed by neutral and protonated cytidines induce the association of cytidine-rich oligonucleotides into parallel duplexes (FIG. 1). Such duplexes are short-lived elusive structures, but the tetramers built by mutual intercalation in head to tail orientation of two hemiprotonated duplexes are extremely stable. This structural arrangement, called i-motif, may include four identical C-rich strands, two hairpins, each caring two cytidine stretches (Nonin et al., 1997) or a folded strand caring four cytidine stretches (Han et al., 1998). The remarkable symmetry of i-motif tetramers is a consequence of the equivalence of the four strands associated in the structure. Face to face intercalation of thymidine in i-motif structures is generally unfavorable (Leroy, 2003; Nonin and Leroy, 1996) and purine intercalation seems to be sterically hindered (Canalia and Leroy, 2005; Canalia and Leroy, 2009; Canalia and Leroy, in press). Recent kinetics investigations suggest that the formation rate of $TC_n$ i-motif tetramers is limited by intercalation of the third strand into a preformed parallel duplex. Structures with partial or optimal intercalation topology are formed at comparable rates and coexist in the early stage of the i-motif build-up. At equilibrium, the predominance of the fully intercalated species is due to its much longer lifetime (Leroy, 2009). I-motifs structures whose lifetime may be as long as years at pH 5 can be dissociated within minutes by a pH shift to neutral pH.

The inventors have now demonstrated that oligonucleotides containing two cytidine stretches separated by a non-cytidine spacer can form i-motif tetramers with incomplete intercalation topology, which constitute efficient building blocks for self-assembly of complex 2-D and 3-D supramolecular structures. Hence, the present invention provides Nanotechnology with a new tool which at least partially overcomes the above-recalled bottlenecks, since it can be used as a nanoscale scaffold which can be modified at will without needing healing-cooling cycles. Advantageously, this new tool is compatible with other nanoscale structures such as proteins, B-DNA or proteo-nucleic structures (PDNA) (Pompon and Laisne, 2007).

The present invention can thus be used to produce DNA nanostructures either alone or together with other molecular or supramolecular structures, in order to obtain complex structures combining the structural properties and the functionalities of each component.

A first aspect of the present invention is hence the use of oligonucleotides of sequences $C_m$—X—$C_n$ (SEQ ID No: 1), to produce supramolecular structures comprising at least 8 oligonucleotides of SEQ ID No: 1, wherein each oligonucleotide is part of an i-motif tetramer. These oligonucleotides have been designed to improve self-assembly of i-motif tetramers into linear or branched supramolecular structures (sms). They consist in two cytidine stretches containing n and m cytidines, wherein m and n are integers comprised between 2 and 7, preferably between 3 and 7. The length of the cytidine stretches may be identical, but they are preferentially different. The longer C stretch may be either at the 5' or the 3' end.

The cytidine stretches are separated by a linker, X formed of one or several (especially 1, 2 or 3) non-cytidine residues which cannot intercalate in a face-to-face orientation into the i-motif structure. The X linker may be selected amongst ribo- or deoxyribo-A, T, G or U nucleotides, modified ribo or deoxyribonucleotides, in particular any functionalized nucleotide derivative allowing the subsequent attachment of a functional component, and diol spacers. A non-limitative example of modified deoxynucleotides which can be used in the present invention is deoxyuracil. Examples of diols which can be used are ethanediol (illustrated in the examples below), or any alcenediol or alcanediol in $C_1$-$C_6$.

Whatever the nature of X, reactive chemical groups can be added to the spacer, in order to facilitate the subsequent attachment of other functional components.

Of course, the present invention also pertains to a supramolecular structure (sms) comprising N $C_m$—X—$C_n$ (SEQ ID No: 1) oligonucleotides, wherein m and n are integers comprised between 2 and 7, preferably between 3 and 7, N is an integer≥8, X is as described above, and wherein each oligonucleotide is part of an i-motif tetramer. By "each oligonucleotide is part of an i-motif tetramer" is meant that each $C_m$—X—$C_n$ (SEQ ID No: 1) is at least partly involved in one or two i-motif tetramers. The smallest supramolecular structure according to the present invention, which is designated as "$Te_2$" in FIG. 2A, consists of 8 oligonucleotides of SEQ ID No: 1, wherein 4 oligonucleotides are part of 2 i-motif tetramers and 4 other oligonucleotides (2 at each extremity of the sms) are part of only one i-motif tertramer.

In a preferred embodiment, n is different from m (n>m or n<m). For example, (m, n) is selected in the group of (4, 7) and (7, 4). As described in the examples below, the nature of the non-cytidine spacer contributes to the dimer stability and therefore interferes with supramolecular structure formation. The experimental data available to date suggest that guanosine (G) and thymidine (T) can advantageously be used as spacers. However, depending on the stability which is wanted, and possibly depending on other constraints, the skilled artisan can chose any other spacer as mentioned above.

Figure 2A:
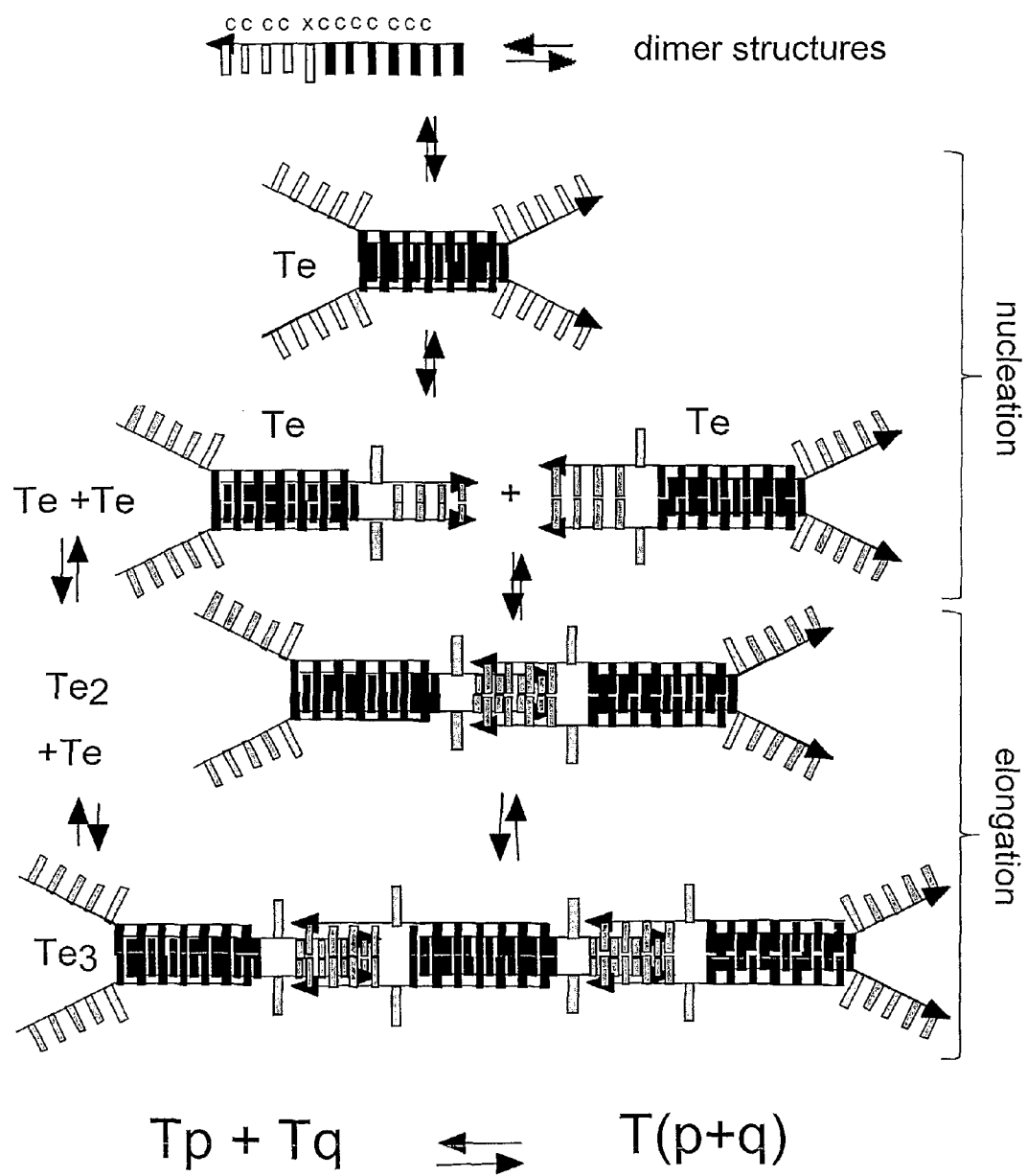

The association pathway of $C_m$—X—$C_n$ oligonucleotides into sms is described in FIG. 2 with the example of sequence $C_7GC_4$ (SEQ ID No: 2). The first step is the formation of the tetrameric building block. The G spacer that cannot intercalate into an i-motif structure prevents intercalation of both cytidine stretches into a single i-motif core. It enforces the formation of a symmetrical tetramer (Te in FIG. 2A) with an i-motif core built by the C·C+ pairs of the longest cytidine stretch terminated at each ends by the two dangling sequences of the shorter C stretch. After the nucleation step, successive associations by pairing and intercalation of the terminal non-intercalated C stretches of two Te building blocks results in formation of $Te_2$, the shortest supramolecular structure according to the invention. The i-motif symetry gives to the assembly of several building blocks the same overhanging terminations of non-paired C as the building blocks themselves. This allows sms elongation by association of pre-formed assemblies containing p and q building blocks (Tp and Tq) into structures including (p+q) building blocks (FIG. 2A) or/and by successive additions of Te buildings. Elongation of supramolecular structures mostly gives rise to linear assemblies. However, time to time three ways branched structures are formed at the junction between I-motif segments, giving rise to a bi- or tri-dimensional network.

Figure 2B:
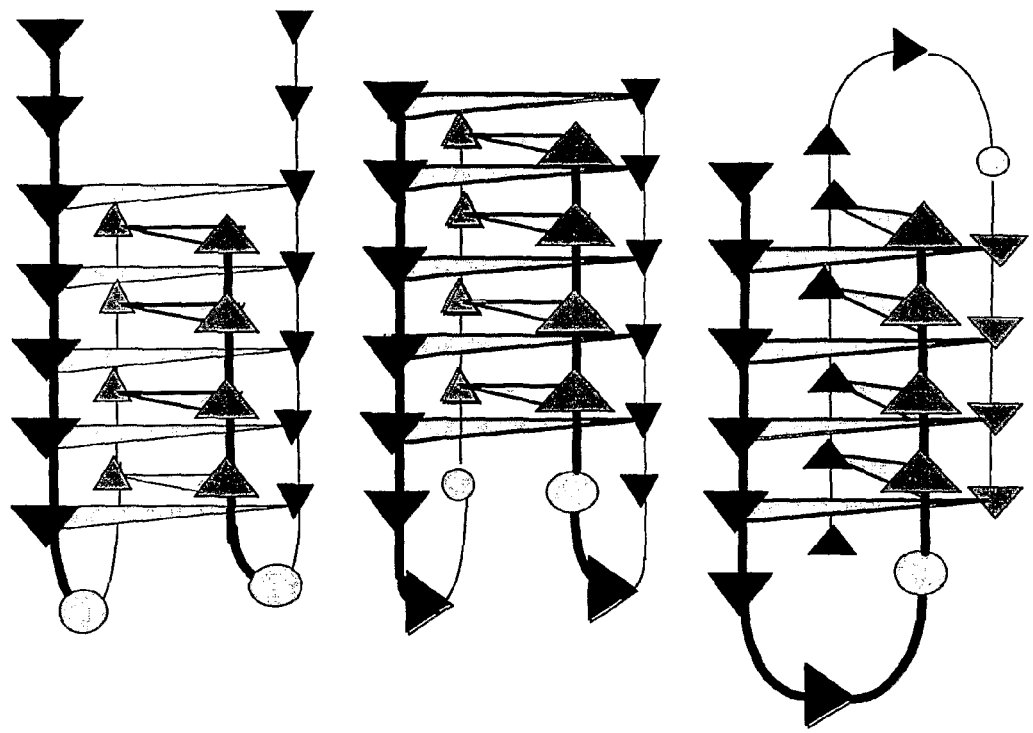

$C_m$—X—$C_n$ oligonucleotides can also associate into dimeric structures by a reaction parallel to that leading to formation of the tetrameric building block Te (FIG. 2A, 2B). $C_m$—X—$C_n$ dimerization hinders sms formation and may be considered as a dead-end way in the sms formation pathway. The dimer formation and dissociation rates depend on the cytidine number (m and n) of the cytidine stretches, on the nature of the X spacer and on physical parameters such as temperature, salt composition and pH. All the factors unfavorable to oligonucleotide dimerization accelerate sms formation and increase the sms length. This is the way by which composition of the $C_m$—X—$C_n$ oligonucleotide influences sms formation. The experimental data available to date show that guanosine (G) or thymidine (T) can advantageously be used as a spacer. Supramolecular structures have been observed with all the $C_4XC_7$ and $C_7XC_4$ oligonucleotides, using X=A, T, G and C2 diol as a spacer, as well as with $C_7TC_3$, $C_3TC_7$, $C_8TC_5$, $C_5TC_5$, $C_5TC_2$, $C_2TC_5$ and $C_3TC_3$.

Atomic force microscopy images show that i-motif sms deposited on a 2-D surface can form either linear structures or a branched bi-dimensional network, according to the experimental conditions and sequence composition (see the experimental section below). The invention includes the formation of these structures.

In a particular embodiment of the invention, the supramolecular structure comprises oligonucleotides having different sequences. The various oligonucleotides comprised in the supramolecular structure can differ either in the lengths of their cytidine stretches, or in the nature of the spacer. For example, a supramolecular structure according to the invention can comprise $C_7GC_4$ (SEQ ID No: 2) and $C_4GC_7$ (SEQ ID No: 3) oligonucleotides, or $C_7GC_4$ (SEQ ID No: 2) and $C_7TC_4$ (SEQ ID No: 4) oligonucleotides, etc. In a particular example described in more details below, the supramolecular structure comprises $C_m$—X—$C_r$, oligonucleotides such as $C_7GC_4$ and terminator oligonucleotides, such as $TC_4$ (SEQ ID No: 7), which associate to the terminal C rich stretches of sms but that cannot provide further elongation. Of course, these examples are not limitative.

As described in the experimental part below, the inventors have obtained monodimensional, bidimensional, tridimensional structures according to the invention. The junctions leading to multidimensional arrangements have not been characterized yet, but they have been observed by atomic force microscopy (FIGS. 15 to 18).

In a preferred embodiment of the supramolecular structure according to the invention, N≥20; more preferably, N≥50.

As mentioned above, supramolecular structures of the invention are compatible with other molecules such as B-DNA, peptides, proteins, proteo-nucleic structures and the like, and can advantageously be combined thereto. Such combinations are also part of the present invention.

The present invention also pertains to a process for producing a supramolecular structure as described above, wherein said process comprises the following steps:

(i) incubating a solution of oligonucleotides of sequence $C_m$—X—$C_n$ (SEQ ID No: 1) as defined above, in a buffer having a pH preferentially in the range 3 to 6; and (ii) obtaining the supramolecular structure.

As described in the examples below, step (ii) can be monitored by gel filtration chromatography or by nuclear magnetic resonance, but the skilled artisan can choose any other convenient technique to follow supramolecular structure formation, such as, for example, atomic force microscopy, surface plasmon resonance, cryomicroscopy, mass spectrometry, electrophoresis, small angle X-ray scattering and light scattering.

As shown in Example 6 below, the sms formation time, which is maximum around the value of the cytidine $pK_{N3}$ (i.e., at pH 4.4), decreases when the pH is shifted away from this value. The mean size of supramolecular structures is maximal at pH 4.4 and decreases at higher and lower pH. Therefore, depending on the characteristics (sms length in particular) which are wished for the supramolecular structures, the skilled artisan will perform the above-described process in the 3 to and 6 pH range, preferably at a pH comprised between 3.5 and 5.5, more preferably between 4 and 5.

The inventors have also demonstrated that the supramolecular structures half formation time decreases when the temperature is increased (Example 4). The incubation step can be performed, for example, at a temperature ranging 15° C. to 65° C.; it will advantageously be performed between 20° C. and 50° C. It is to be noted that, absent other parameters changes, the sms formed at 20° C. will be larger in size, but will appear more slowly, than those obtained at higher temperatures.

Another parameter influencing supramolecular structure formation is the oligonucleotide concentration. Indeed, the sms half formation time decreases as the inverse of the oligonucleotide concentration and it has been observed that the oligonucleotide fraction incorporated in sms and the sms length increase with the oligonucleotide concentration (Example 5). When performing the process according to the invention, the oligonucleotide will advantageously be used at a concentration larger than 50 µM, the oligonucleotide concentration for which 50% of a $C_7GC_4$ (SEQ ID No: 2) solution is associated is sms at equilibrium in a pH 4.6 solution at 42° C.

According to a preferred embodiment illustrated in the examples below, the buffer used for the incubation step comprises 0.4 M NaCl, 10 mM sodium acetate and 10 mM sodium phosphate.

In order to reach the equilibrium, or at least a satisfactory sms proportion, the incubation step is preferably performed during at least 30 minutes, preferably at least 1 hour. Depending on the various parameters (oligonucleotide sequence and concentration, pH, temperature, etc.) the equilibrium can necessitate a longer incubation (up to 50-100 hours or even more) to be reached.

In a particular embodiment illustrated in examples 1 to 9 below, the supramolecular structure is obtained in step (ii) in the buffer solution. Once the sms is obtained, the skilled artisan can choose to cool the solution containing it, or to change its pH or composition, or to remove the sms from the solution (for example, by chromatography or electrophoresis). Elongation can also be stopped by adding an excess of a "terminator oligonucleotide", i.e., an oligonucleotide that associates to the terminal C-rich stretches of sms but that cannot provide further elongation. Examples of terminator oligonucleotides comprise a first moiety consisting of a C stretch (for example $C_4$, $C_5$, $C_6$, $C_7$ or $C_8$) and a second moiety comprising one to 10 nucleotide(s) without any C stretch ($C_pX$, with p=3 to 8 and X=A, T, G, U, a modified nucleotide as described above or a chemical group such as an alcanol or X=one to 10 nucleotides, modified or not, with the proviso that X does not comprise a C stretch of at least two consecutive cytosine residues (SEQ ID No: 6)). For example, elongation of the sms of $C_7GC_4$ (SEQ ID No: 2) in FIG. 1 can be stopped by addition of $TC_4$ (SEQ ID No: 7), an oligonucleotide whose $C_4$ stretch can intercalate into the dangling $C_4$ terminations of the sms but whose terminal T has no further elongation capacity. It is noteworthy that terminators with a reactive group such as biotin provide sms binding to any other polymer, to surface or bead supports labeled with the appropriate reactive group. Non-limitative examples of reactive group that can be used in this context are steptavidin, digoxigenine, amino and thiol linkers, . . . . Hence, such terminators can also enable easy association to other type of molecular components like B-DNA, proteins, peptides or any other polymer.

Alternatively, as described in Example 10 below, the supramolecular structure can be obtained by self-assembly in the presence of a surface able to non-covalently bind DNA. In such a case, the sms wil be obtained on said surface. The sms obtained in step (ii) is then a 2D structure, or 3D if said surface is 3-dimensional. Of course, the technical approaches described above to terminate sms formation and/or stabilize the obtained sms (temperature, pH or buffer change, or use of terminator oligonucleotides) can also be used when self-assembly is performed on a surface.

Another aspect of the present invention is related to the dissociation process of supramolecular structures. According to this aspect, the present invention pertains to a process for dissociating a supramolecular structure as defined above, comprising a step of changing the pH of the environment of said supramolecular structure. Indeed, the i-motif stability is highly pH-dependent, and a limited pH shift, for example from pH=6 to pH=6.5 or pH=7, results in dissociation of the structure (with, of course, a quicker dissociation at pH=7 than 6.5). This sensibility of i-motif link stability to pH (from fraction of second to several years life time) enables a very simple approach for self-repair or default removal based on sequential destabilization a pre-establish network by pH shift, followed by spontaneous exchange or relocation of damaged or incorrectly located blocks and self-ligation before final restoration of the overall network stability by a reverse pH shift. Dynamic programming by transient and reversible pH shift can also be performed. This property is also extremely interesting in supramolecular structures including i-motif elements and elements which are stable at pH 7 (B-DNA or G-quartet elements, for example). A pH jump from typically 6 up to 7, would induce in that case a conformational change in a physiological range of pH. When the sms are associated to a surface, the pH change can be spatially limited and induce only localized reorganization of the structure. Such local change can be performed by known methods like the attachment to the surface of photoactivated bases or acids.

Other characteristics of the invention will also become apparent in the course of the description which follows of the experimental assays which have been performed in the framework of the invention and which provide it with the required experimental support, without limiting its scope.

LEGENDS TO THE FIGURES

FIG. 1: i-motif tetramers. A. Hemiprotonated C·C+ pair formed by neutral and protonated cytidines. B. Schematic representation of the i-motif tetramer formed by association of four TCCCCC (SEQ ID No: 8) soligonucleotides. C (top). Schematic representation of the hemiprotonated parallel duplex of CC. C (bottom). i-motif tetramer of CC. The tetramer is stable whereas the hemiprotonated parallel duplex is a short lived structure in fast exchange with the CC monomer. D. High resolution structure of the $[CC]_4$ i-motif. The views are normal to the wide and narrow grooves. The background residues are drawn in thin line.

FIG. 2: A. Postulated association pathway of $C_7GC_4$ (SEQ ID No: 2) into sms. The cytidines of the $C_7$ and $C_4$ stretches are represented by black and t gray triangles, respectively. The guanosine linker connecting the two C stretches is represented by a gray slab. The monomer is in equilibrium with a hairpin dimer (Cf. FIG. 2B) and Te, the tetramer formed by full intercalation of the $C_7$ stretch. Te includes an i-motif core formed by pairing and stacking of the cytidines of the longer C-stretch and two dangling $C_4$ stretches at each end. Mutual intercalation of the C·C$^+$ pairs of the $C_4$ stretches of two Te building blocks results in the formation of the Te$_a$ species. Stacking of the outer C·C$^+$ pair of the $C_7$ i-motif core (black block) with the outer pair of the $C_4$ core (striped block) is presumably favorable to the stability of the assembly of two building blocks. The i-motif symmetry gives to the assembly of several building blocks the same elongation capacity than the building blocks themselves and allows the association of preformed Te$_p$ and Te$_g$ species into a structure including (p+q) building blocks. B. Plausible structures of the $C_7XC_4$ (SEQ ID No: 9) dimer (X=A, T or G). The structures optimize the number of intercalated C·C$^+$ pairs. The narrow (n) and wide (w) grooves are indicated on structure a. One residue is enough to make a loop across the i-motif narrow groove (Canalia and Leroy, 2005). Three residues allow loop formation across the wide groove (Leroy, 2003). For each loop topology, the hairpins may be in parallel (a,c) or in head to tail orientation. (b,d). Many other topologies can be imagined by changing the intercalation order of the C·C+ pairs and the number of residues in the loops. The poor resolution of the NMR spectrum of $C_7GC_4$ (SEQ ID No: 2) suggests that several dimers coexist.

Figure 3:
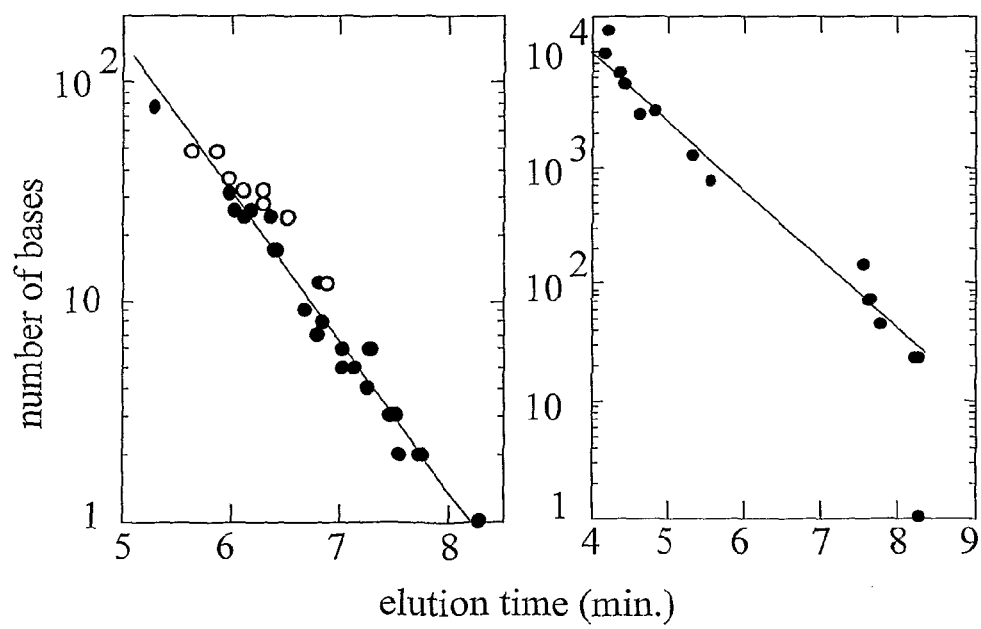

FIG. 3: Calibration curves of the GPC 100 (left panel) and GPC 1000 (right panel) gel filtration columns used to determine the sms molecular weight and the multimer stoichiometry of $C_mXC_n$ (SEQ ID No: 1) i-motif assemblies. The GPC 100 column was calibrated with tRNA, thymidine, C-rich i-motif monomers, non-structured C-rich oligonucleotide (black dots) and i-motif tetramers characterized in previous NMR investigations (open dots). The data points corresponding to structured or non-structured oligonucleotide families do not show significant deviation indicating a marked influence of the oligonucleotide structure. The GPC 1000 column was calibrated with double stranded plasmids.

Figure 4:
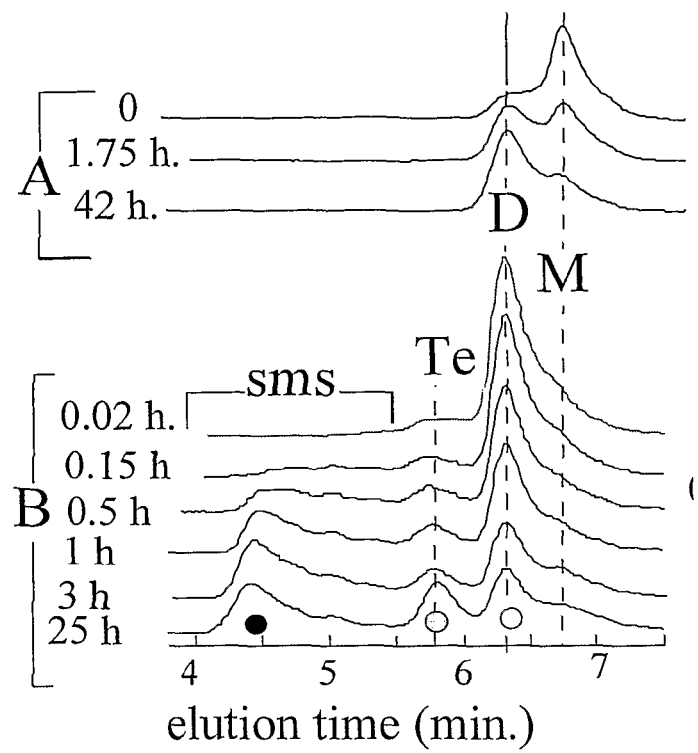
Figure 4:
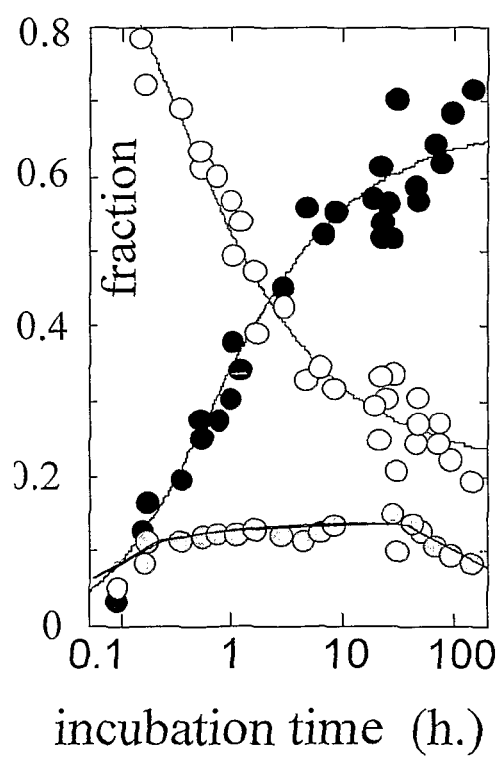

FIG. 4: Association of $C_7GC_4$ (SEQ ID No: 2) into i-motif multimers and supra molecular structures (sms). Upper panel: GPC-100 chromatograms of $C_7GC_4$ (SEQ ID No: 2) samples recorded after incubation during the times indicated on the figure. The elution time expected for a monomer (M), a dimer (D), and a tetramer (T) are indicated. A: the chromatogram of a 3 mM solution, pH 6.2 injected right after melting shows a 20/80 dimer/monomer mixture. The monomer and dimer concentrations at equilibrium correspond to the reduced dissociation constant; $Fi_{dimer}=2$ mM. B: The chromatograms of a 0.15 mM $C_7GC_4$ (SEQ ID No: 2) solution at pH 4.63 collected after melting and incubation at 50° C. during the times indicated on the figure show that the dimer is slowly converted into tetramer and supra-molecular structures. Lower panel: evolution of the sms (black circles), tetramer (grey circles) and dimer (open circles) fraction as a function of the incubation time at 50° C.

Figure 5:
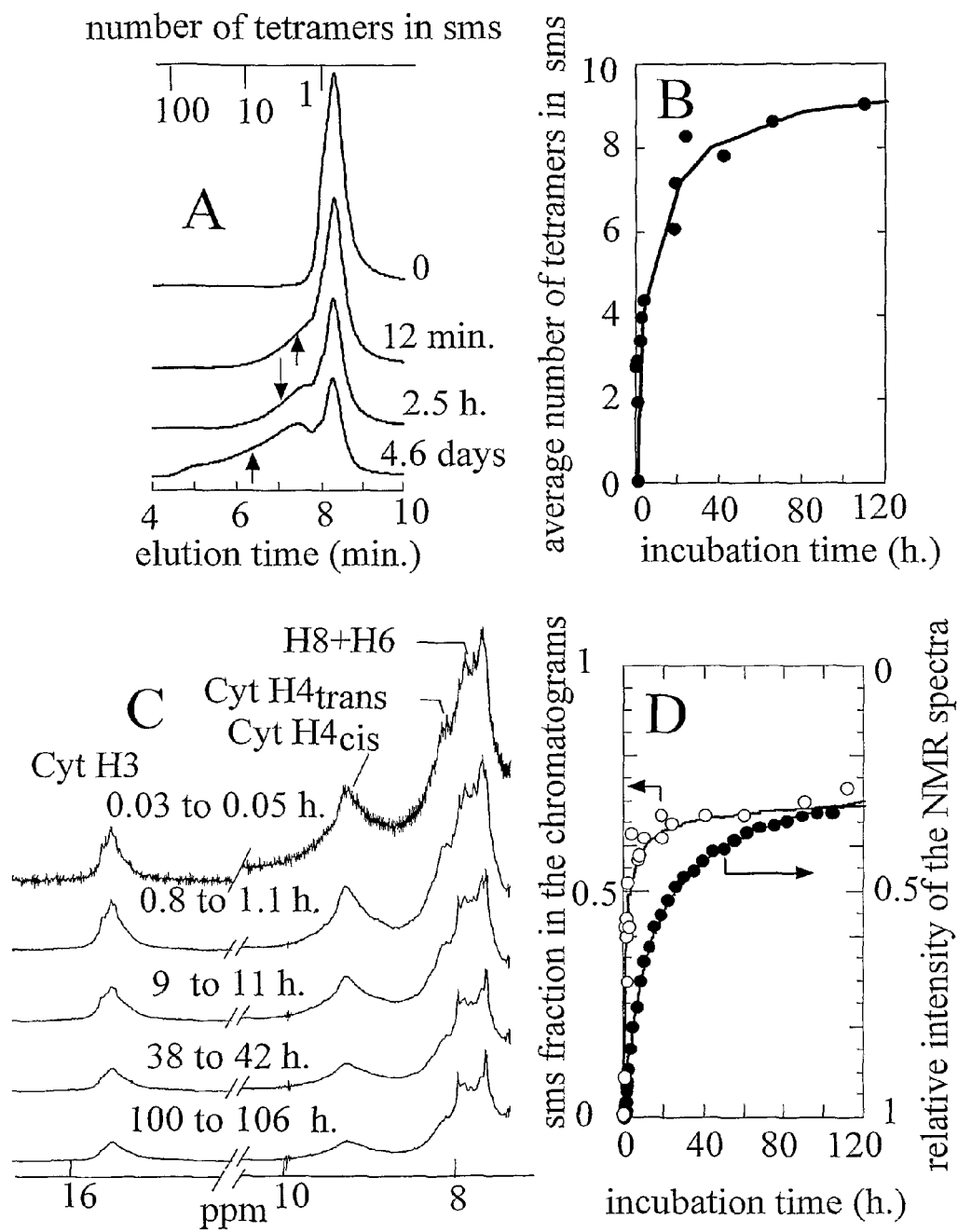

FIG. 5: Association of $C_7GC_4$ (SEQ ID No: 2) into sms as monitored by gel exclusion chromatography on GPC 1000 column and NMR. The oligonucleotide was initially melted. The NMR spectra and the chromatograms were recorded after incubation at 37° C. at the times indicated. Solution conditions: $[C_7GC_4]=1.5$ mM, pH=4.6. Panel A. The peak of chromatogram collected at t=0 corresponds to the unresolved tetramer and dimer. The chromatograms collected as a function of the time show the formation of sms. According to the calibration curve of FIG. 3, the upper scale gives the correspondence between the elution times and number of tetrameric repeats associated in the sms. Note that one tetrameric repeat contains 4×12 residues. An arrow indicates the center of the sms distribution on each chromatogram. Panel B. the number of tetramer repeats at the center of the sms distribution is plotted as a function of the incubation time. At equilibrium, the average molecular weight of sms corresponds to the association of 9 tetramers (i.e., 432 bases). The top 15% of the sms distribution includes structures that are 5 times larger. Panel C. exchangeable and aromatic proton region of the NMR spectra collected during sms formation. The line broadening (about 40 Hz) and the reduction of the signal intensity observed as a function of the time reflect the formation of large structures. Panel D. oligonucleotide fraction included in sms as determined from the chromatograms of panel A (open circles) and from the intensity of the NMR peaks as determined from panel C (black circles). The time constant derived from the chromatography measurements, 1 hour, concerns the formation of structure heavier than a tetramer whereas that derived from the NMR experiments, 20 hours, is related to structure that are too large to be detected on the NMR spectrum.

Figure 6:
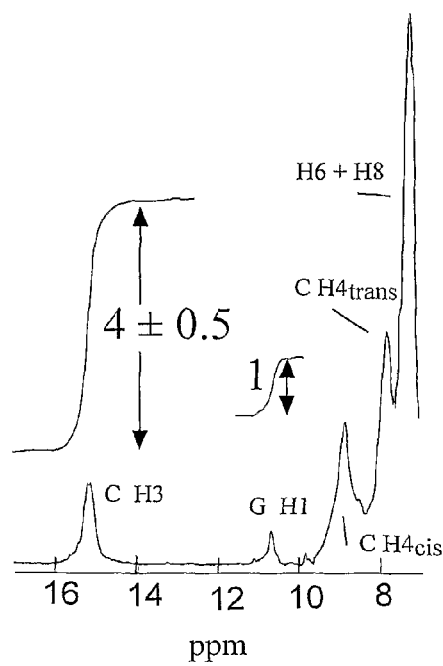

FIG. 6: Exchangeable and aromatic proton region of a 1.5 mM $C_7GC_4$ (SEQ ID No: 2) solution pH 4.6. The spectrum was recorded at 0° C. about 2 minutes after melting and fast cooling. The area of the imino proton peak is about 4 times larger than that of the G imino proton, a value consistent with the structures displayed in FIG. 2B.

Figure 7:
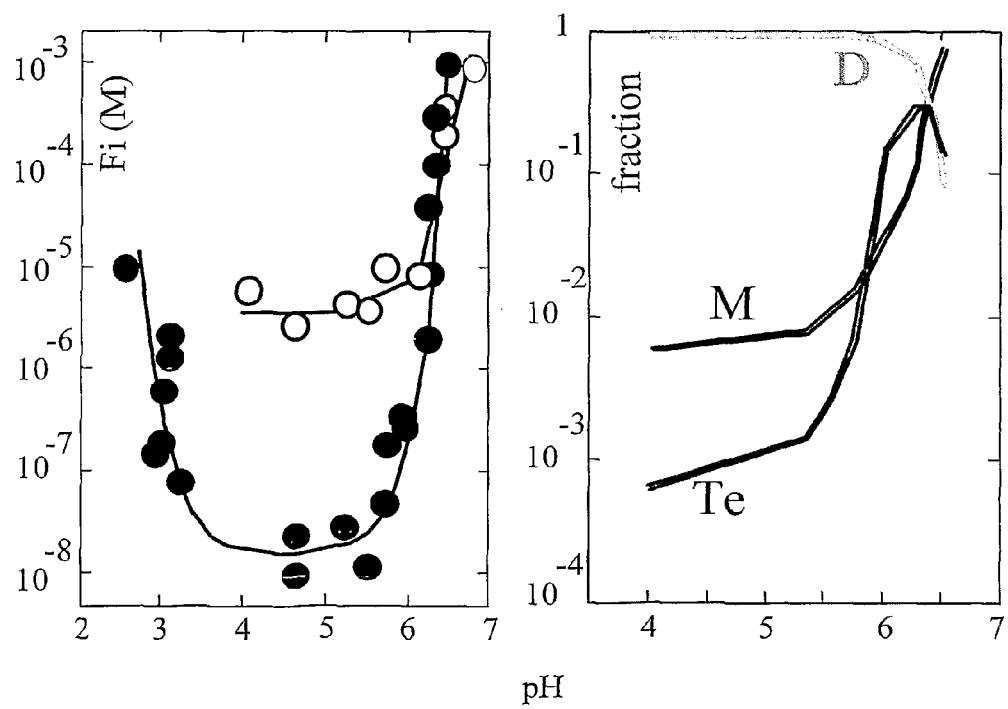

FIG. 7: Effect of pH on dimer and tetramer stability. Left panel: reduced dissociation constant of $[C_7GC_4]_2$ (black circles) and $[C_7T]_4$ (open circles) vs. pH. $C_7T$ (SEQ ID No: 10) do not associate into dimer or sms. It was used as a model to estimate the stability of the tetramer of $C_7GC_4$ (SEQ ID No: 2) formed by pairing and intercalation of the cytidine of the longer C stretch, which is assumed to be the building blocks of the sms elongation pathway (Te in FIG. 2A). Right panel: computed monomer (M), dimer (D) and tetramer (Te) fractions in a 0.3 mM $C_7GC_4$ (SEQ ID No: 2) solution assuming that the tetramer of $[C_7GC_4]_4$ has the same reduced dissociation constant than $[C_7T]_4$. Due to the greater sensitivity of the dimer stability to pH, the tetramer fraction increases by two magnitude orders between pH 5.5 and pH 6.2 (Canalia and Leroy, 2005).

Figure 8:
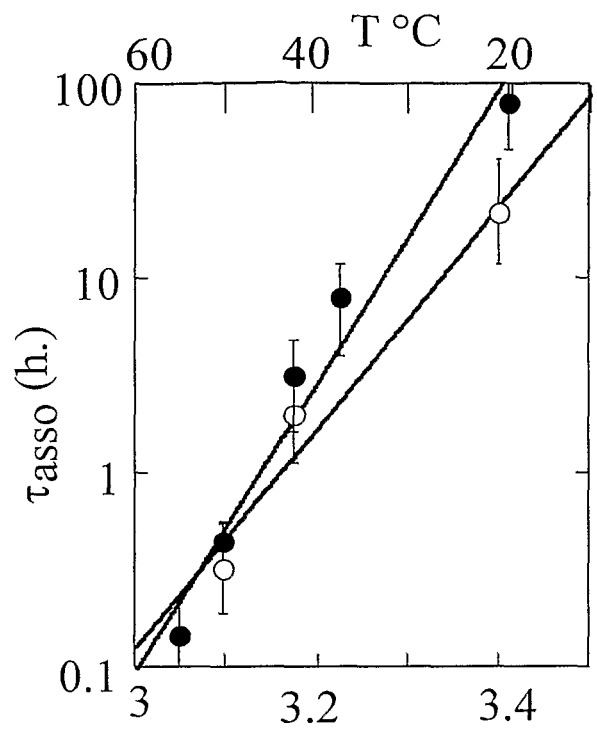

FIG. 8: Sms half formation times vs. temperature in 0.3 mM $C_7GC_4$ (SEQ ID No: 2) (black circles) and $C_4GC_7$ (SEQ ID No: 3) (open circle) solutions at pH 4.6. The activation energies related to sms formation, 143±40 and 110±25 kJ/M are comparable.

Figure 9:
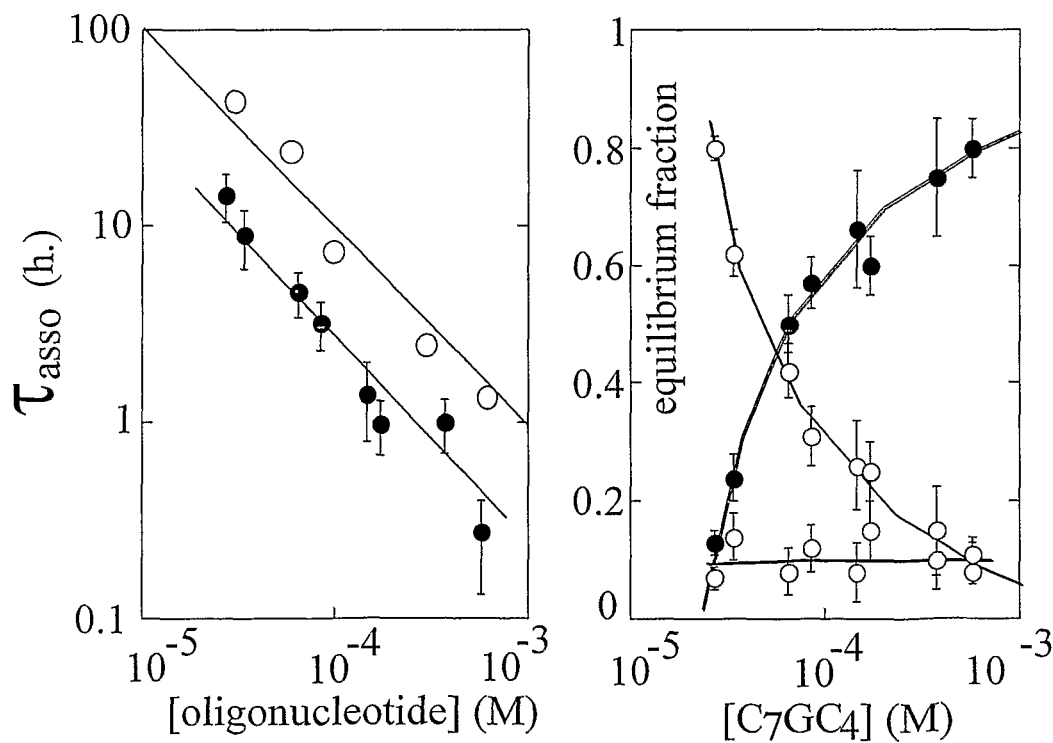

FIG. 9: Effect of the oligonucleotide concentration on the sms half formation time at 42° C., pH 4.6. Left panel: sms half formation time vs. the oligonucleotide concentration in $C_7GC_4$ (SEQ ID No: 2) (black circle) and $C_4TC_7$ (SEQ ID No: 5) (open circles) solutions. The slope of the lines drawn through the data points is −1. Right panel: dimer (open circles), tetramer (grey circles) and sms (black circles) equilibrium fractions vs. the oligonucleotide concentration. The monomer concentration is negligible in this range of concentrations.

Figure 10:
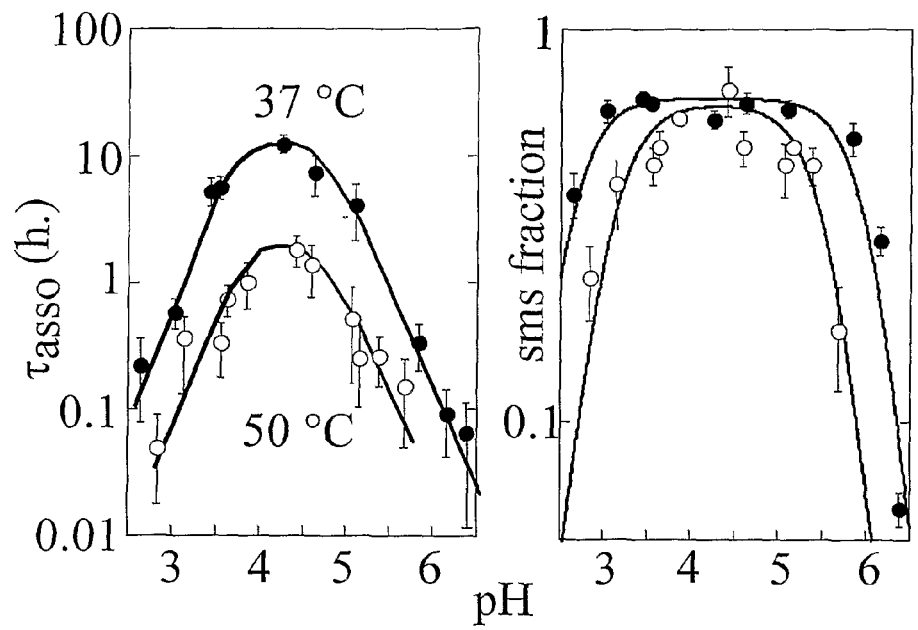

FIG. 10: Effect of pH on sms formation in 0.3 mM $C_7GC_4$ (SEQ ID No: 2) solutions at 37 (black circles) and 50° C. (open circles). Left panel: sms half formation time vs. pH. The sms formation time is maximal when the pH is equal to the cytidine $pK_{N3}$. Right panel: The oligonucleotide fraction incorporated at equilibrium into sms at 37 and 50° C. vs. pH.

Figure 11:
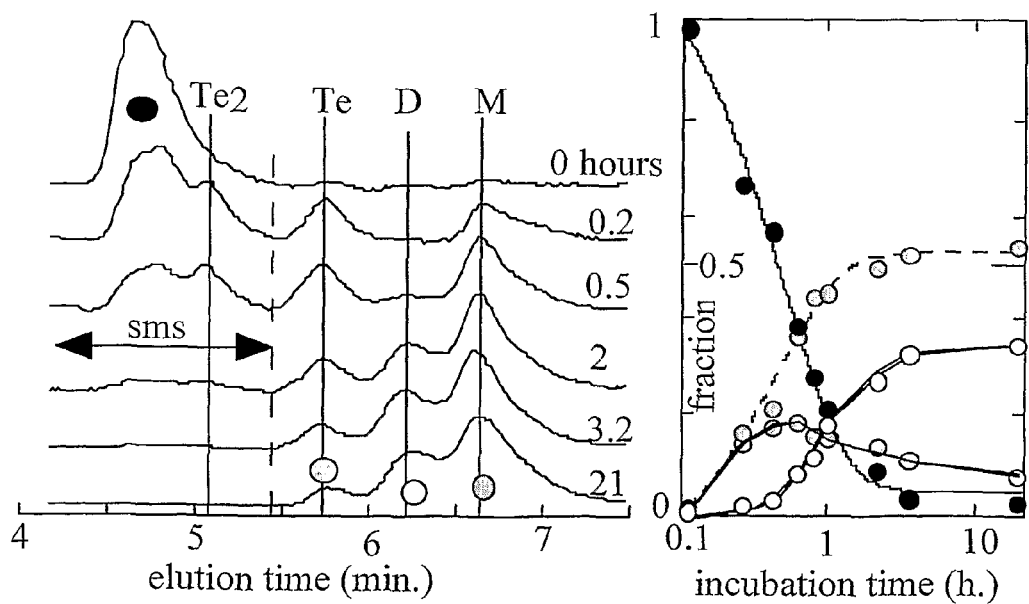

FIG. 11: Dissociation of the sms of $C_7GC_4$ (SEQ ID No: 2) at 40° C., pH 4.63. Left panel: The chromatograms of a 3 mM solution recorded as a function of the time show that sms dissociation first results in the formation of tetramer (Te) and of $Te_2$, a species whose elution time corresponds to that expected for the assembly of two tetramers and of monomer (M). At last the chromatogram shows the formation of a dimer (D). Note that the dimer fraction increases with an initial zero slope. Right panel: evolution of the Te (grey circles), D (open circles), M (striped circles) and sms (black circles) fractions as the function of the time.

Figure 12:
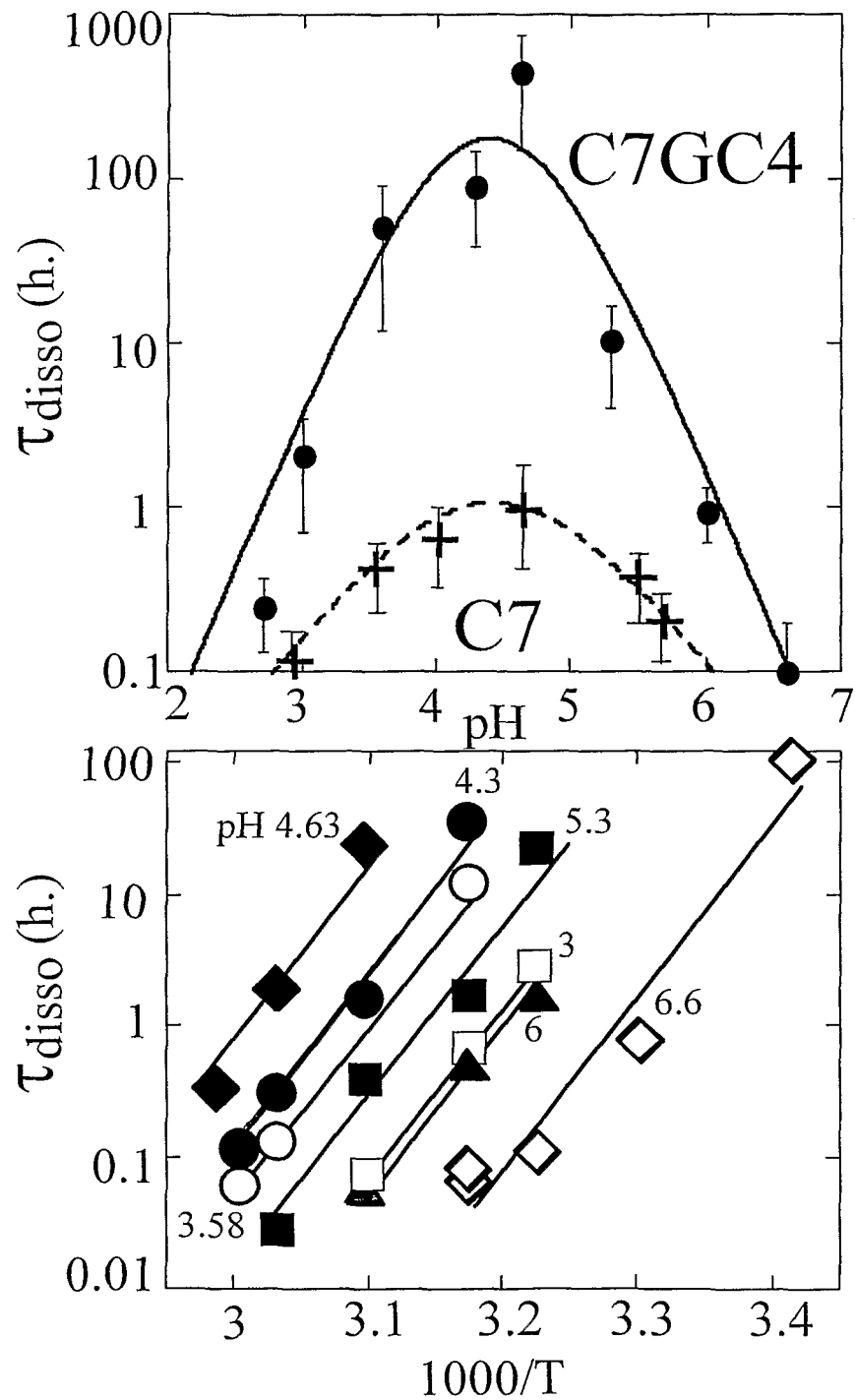

FIG. 12: Effect of pH and temperature on the sms lifetime. Lower panel: half dissociation time of the sms of $C_7GC_4$ (SEQ ID No: 2) vs. temperature at pH 4.63 (black diamonds), pH 4.3 (black circles), pH 3.58 (open circles), pH 5.3 (black squares), pH 3 (open squares), pH 6 (black triangles) and pH 6.6 (open diamond). Upper panel: lifetimes at 40° C. vs. pH of the sms formed by $C_7GC_4$ (SEQ ID No: 2) (open circles) and $C_7$ (crosses). The sms lifetime is maximal when the pH is equal to the cytidine $pK_{N3}$ and decreases at lower or upper pH.

Figure 13:
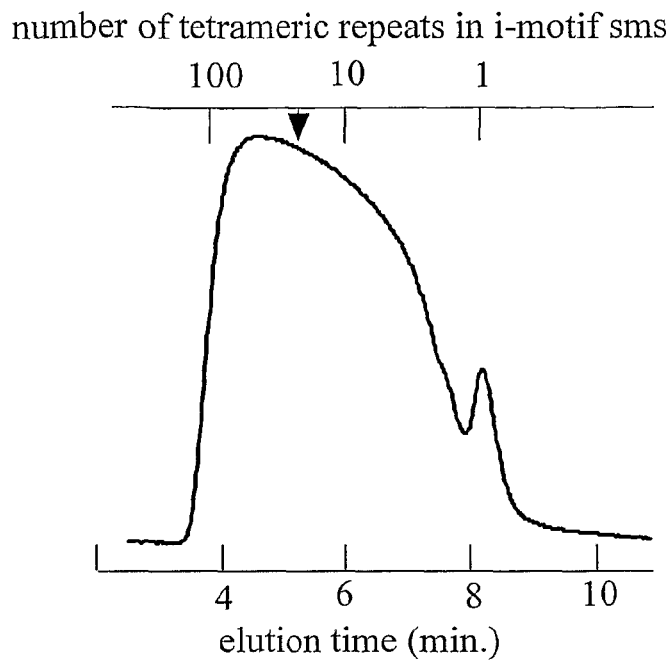

FIG. 13: GPC 1000 chromatogram of a 4.4 mM $C_4GC_7$ (SEQ ID No: 3) solution pH 4.6 incubated at 42° C. during 68 h. 90% of oligonucleotide is associated in sms. An arrow indicates the center of the sms distribution. It corresponds to a molecular weight equivalent to that of 25 tetramers (i.e. 1800 residues). 5% of the sms include more than 90 tetramers.

Figure 14:
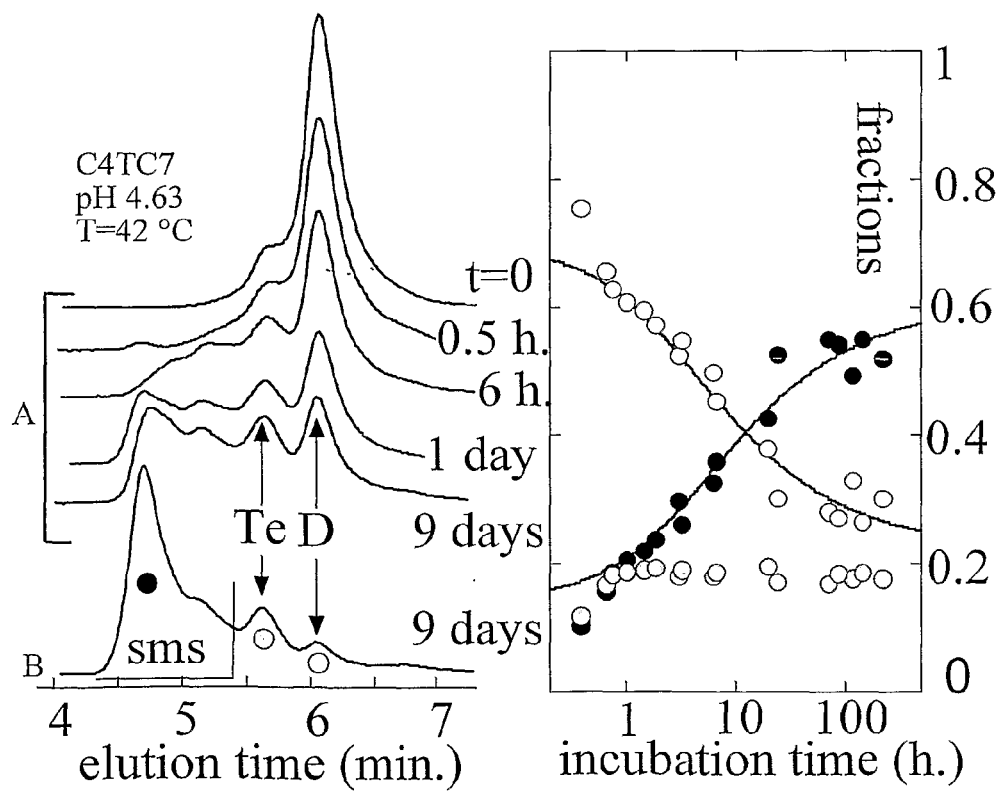

FIG. 14: $C_4TC_7$ (SEQ ID No: 5) association into sms at 42° C., pH 4.6. Left panel: Chromatograms of 0.3 mM (B) and 3 mM (A) solutions recorded after incubation during the times indicated on the figure. The elution times expected for the dimer and tetramer of $C_4TC_7$ (SEQ ID No: 5) are labeled D and Te. Right panel: Evolution of the dimer (white), tetramer (grey) and sms (black) fractions as a function of the incubation time. At equilibrium, the oligonucleotide fractions associated in sms are 60% and 80% in 0.3 mM and 3 mM solutions respectively FIG. 15: Atomic force microscopy image of sms on mica in the conditions described on example 10 of self-assembled $C_7TC_4$ (SEQ ID No: 4) oligonucleotides. A) Example of linear structures. B) Branched bi-dimensional network (1 μm full scale).

Figure 16:
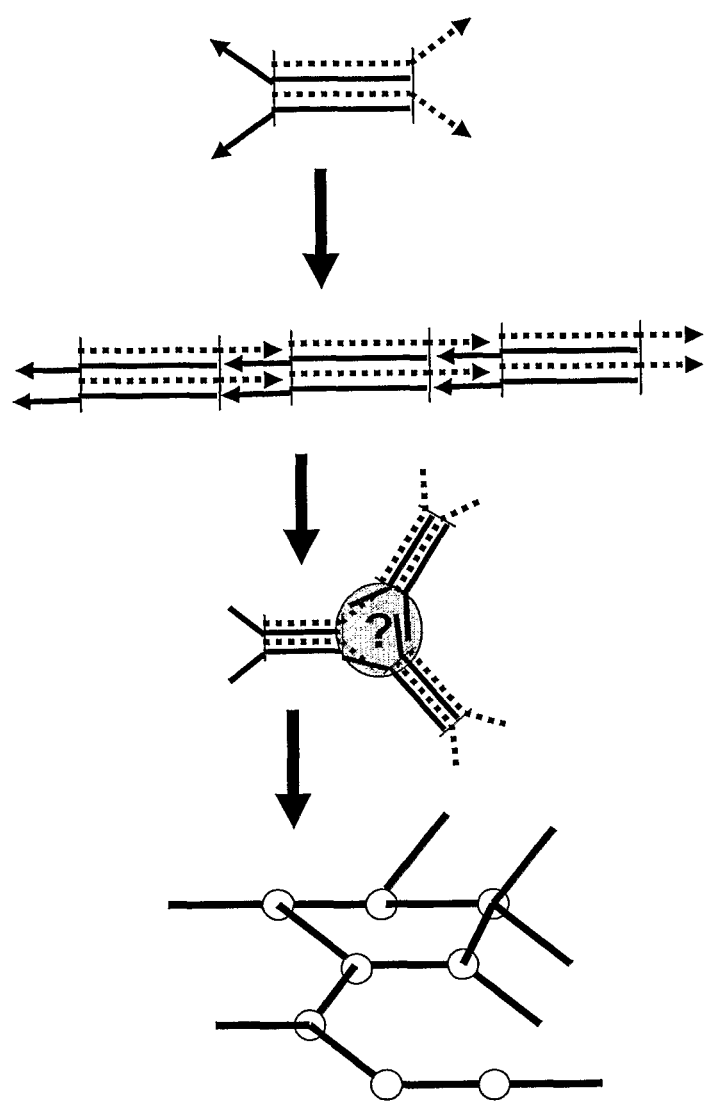

FIG. 16: Schematic representation of linear and branched self-assembly mode of I-motif based sms.

Figure 17:
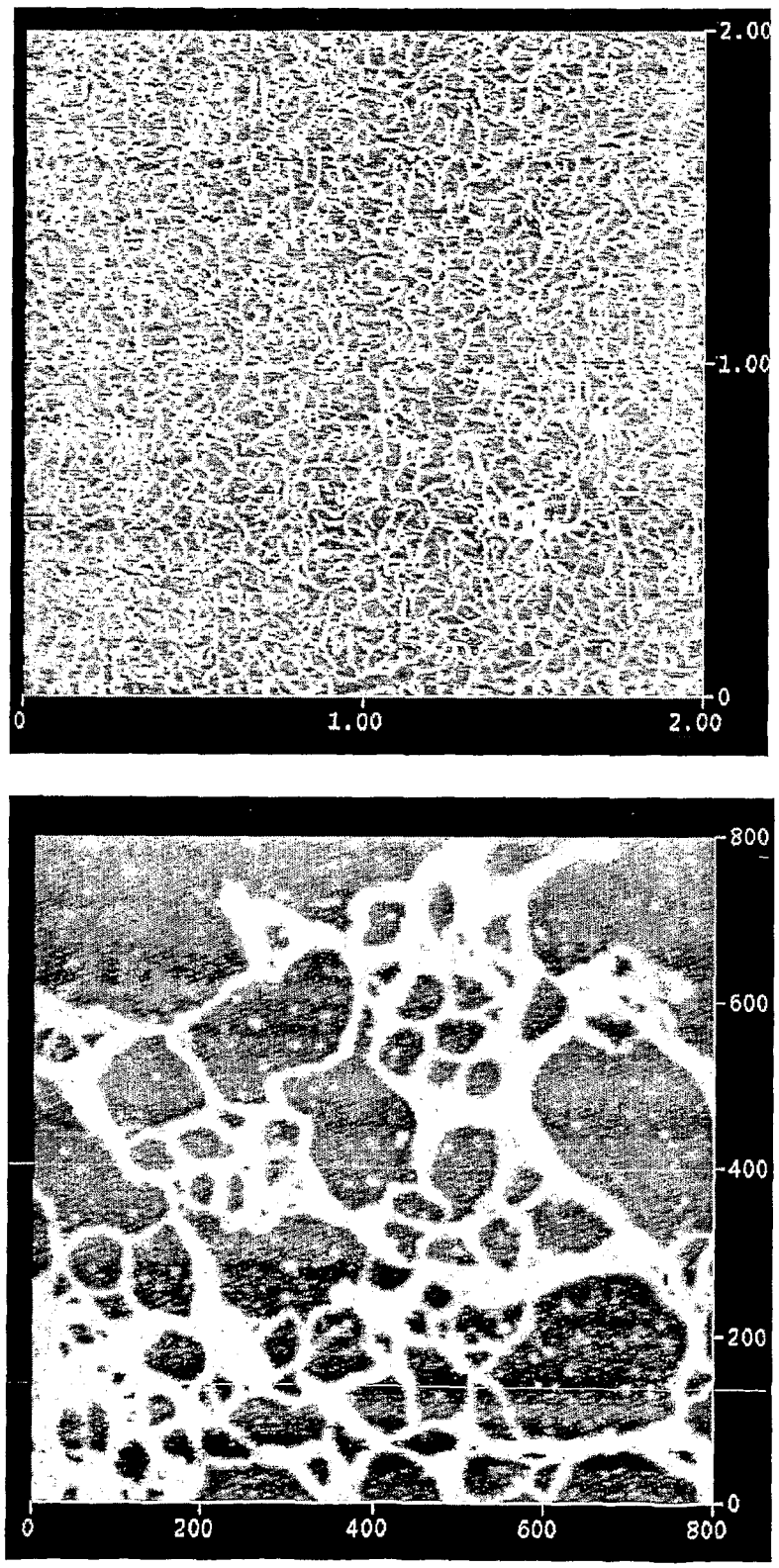

FIG. 17: Atomic force microscopy image of sms on mica in the condition described on example 10 of self-assembled C7TC4 oligonucleotides. Top: Same sample as in FIG. 15 but with a different scale (4 μm full scale). Bottom: Other sample deposited using a larger dilution (800 nm full scale).

Figure 18:
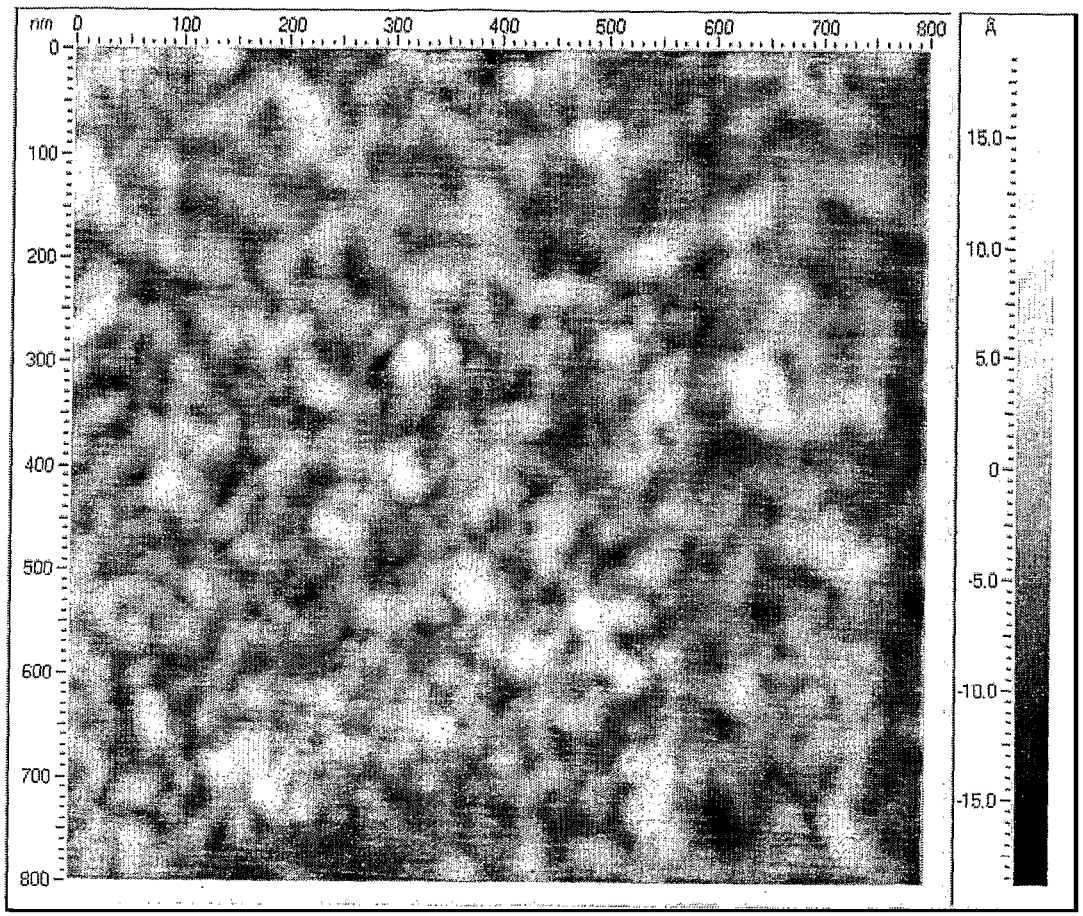

FIG. 18: Atomic force microscopy image of the shapeless pellets formed by the self-assembly of $C_7GC_4$ oligonucleotides (8 μm full scale).

EXAMPLES

All the experiments described below have been performed with the following materials and methods.

Oligonucleotide Synthesis and Sample Preparation

The oligonucleotides were synthesized on a 2 or 10 μM scale, purified by chromatography on an anionic DEAE column according to procedures already described, and extensively dialyzed (Leroy, 2003). After dialysis, the oligonucleotide solutions were lyophilized and dissolved in water to make 0.5 to 1 mM stock solutions. The solution pH was adjusted to 4.6 with NaOH or HCl. The $C_7GC_4$ (SEQ ID No: 2) concentration was determined using the $A_{260}$ values, 89600 $M^{-1}$ $cm^{-1}$, computed according to a nearest neighbor model (Cantor et al., 1970).

Formation and Dissociation Rate Measurements of i-Motif Sms

All the measurements were performed in a 0.4 M NaCl solution buffered by 10 mM Na acetate and 10 mM Na phosphate that will be designed hereafter as the NAP buffer. During sms formation and dissociation, the samples, typically 50 to 200 were incubated in a mastercycler Eppendhorf® PCR incubator whose lid temperature was set 5° C. above that of the samples in order to avoid top condensation.

To measure the sms formation kinetics, the samples were initially melted at 100° C. and rapidly cooled at the temperature of the incubator. To measure the sms dissociation time, a solution containing only sms was prepared by pooling the multimers eluted on a GPC 100 column with a molecular weight larger than that of a tetramer. Afterward, this solution was diluted in the NAP buffer in such way as to allow full dissociation of the sms at equilibrium. The dissociation kinetic measurements started right after dilution.

Gel Filtration Chromatography

The evolution of the monomer and multimer fractions during sms formation and dissociation was measured at room temperature by gel filtration chromatography on GPC 100 and GPC 1000 columns (250×4.6 mm I.D.) provided by Eprogen®, using the NAP buffer as elution solution with a flow rate of 0.4 ml/min. Aliquot took off the incubated samples were injected in the column after dilution to 25 μl (the volume of the injection loop) in the NAP buffer. Systematic addition of thymidine to a final concentration of about 5 μM to the injected sample provided a reference marker on the chromatograms. The elution times ranged from 4 to 9 min (FIG. 3). The pH of the elution buffer was generally 4.6. However, when the evolution of the sample composition during elution on the columns at pH 4.6 was not negligible, the pH of the NAP buffer was adjusted to the same value than the sample during incubation. The exclusion limit of the GPC 100 column corresponds, according to the manufacturer, to an oligonucleotide containing about 300 nucleotides. The column was calibrated using tRNA, thymidine, C-rich i-motif monomers, C-rich non-structured oligonucleotides and i-motif tetramers. For the GPC-1000 column, double stranded plasmids containing from 800 to 16000 nucleosides were used. The permeation and exclusion limits of the GPC-1000 column correspond to oligonucleotides of about 50 and 104 nucleotides, respectively. The molecular weight of the structures formed by association of the C-rich tetramer was determined by reference to the calibration curves displayed in FIG. 3. The dimer and tetramer stoichiometries were also routinely measured by the slope on a log-log scale of the plot of the multimer vs. monomer concentrations at equilibrium.

In pH and temperature conditions favorable to sms formation, an opalescence characteristic of the formation of extremely large structures was observed in concentrated samples (>1 mM) incubated during a time much longer than the time constant for sms formation. Correlatively with the sample opalescence, the chromatogram of these samples showed a reduction (up to 50%) of the integrated area of the eluted species, indicating that a fraction of the sample, composed presumably of the largest sms, was trapped in the gel filtration column. In that case, the oligonucleotide fraction retained on the column was estimated by comparison with the chromatogram of an identical melted sample. However, the inventors generally restrained the oligonucleotide concentrations and incubation times to a range of values allowing detection of all the species on the chromatograms.

The Multimers Dissociation Constant

The dissociation constant of a multimer may be expressed as a function of $\alpha_{eq}$, the monomer equilibrium fraction of an oligonucleotide solution at concentration $[M_0]$ by: $K_{dis}=s\alpha_{eq}^s\cdot[M_0]^{s-1}/(1-\alpha_{eq})$, where s is the multimer stoichiometry.

The multimers stability is characterized by Fi, a parameter independent of the stoichiometry, equal to the free monomer concentration for which $\alpha_{eq}=0.5$.

Fi, which is herein designated as the reduced dissociation constant, is related to the multimer dissociation constant by: $Fi=(K_{dis}/s)^{(1/(s-1))}$.

NMR Method

The NMR experiments were performed using a 500 MHz Varian Inova spectrometer with the jump and return sequence for water suppression (Plateau and Guéron, 1982). The spectral intensity was multiplied by a 1/sin function in order to correct the intensity distortion introduced by the jump and return excitation (Guéron et al., 1991). The spectra are scaled by reference to DSS whose methyl peak was set at 0 ppm.

Example 1

Chromatographic Evidence for the Formation of i-Motif Supramolecular Structures

Immediately after melting and fast cooling, the chromatogram of a 3 μM $C_7GC_4$ (SEQ ID No: 2) solution, pH 6.2 injected into a GPC 100 column is mainly eluted as a monomer (FIG. 4). The chromatograms recorded at different times during incubation at 20° C. reveal that a dimer is formed with a time constant of about 1.5 hours. At equilibrium, the dimer and monomer concentrations correspond to the reduced dissociation constant Fi=μM. It has been shown that the formation rate of i-motif dimers increases as the nucleotide concentration and when the solution pH is shifted near 4.4, the value of the cytidine $pK_{N3}$ (Leroy, 2009). This explains that about 1 min. after melting, a 0.15 mM $C_7GC_4$ (SEQ ID No: 2) solution, pH 4.6 is eluted as a dimer (FIG. 4). The chromatograms recorded at different times during incubation at 50° C. show the formation of a tetramer and of larger structures that are eluted in an unresolved peak. All the species eluted with a molecular weight larger than that of a tetramer will be henceforth designated as supramolecular structures (sms). The evolution vs. time of the dimer, tetramer and sms fractions is displayed in FIG. 4. The tetramer fraction reaches after 0.5 h a maximum value of about 12% and the sms fraction increases towards an equilibrium level of 65% with a time constant of 1 hour. The dimer fraction decreases with a comparable time constant. The molecular weight of the sms was estimated using a GPC-1000 column. The chromatograms of aliquots taken from a 1.5 mM $C_7GC_4$ (SEQ ID No: 2) solution incubated at 37° C., pH 4.6 are displayed in FIG. 5A. The dimer and the tetramer are eluted as a single peak in the permeation volume of the column. The sms half formation time is 1 h and the oligonucleotide fraction associated in sms at equilibrium is about 75% (FIG. 5D). The average size of the sms increases as a function of the incubation time (FIG. 5B). After incubation during four days at 37° C., the sms exhibited an extremely broad distribution centered around 430 residues, a size corresponding to the association of 9 tetramers. The elution time of the largest species, 4.5 min., is that expected for structures including about 4000 residues, i.e. 80 tetrameric units.

Example 2

Sms Formation Monitored by NMR

Right after melting and fast cooling at 0° C., the NMR spectrum of $C_7GC_4$ (SEQ ID No: 2) shows three broad clusters of exchangeable protons at the positions characteristic of the imino and amino protons of C·C+ pairs (Leroy et al., 1993). The poor spectral resolution suggests the presence of multiple conformations (FIG. 6). The 10.3 ppm chemical shift and the fast exchange rate of the G imino proton indicate that the guanine is not H bonded to a cytidine. The intensity of the cytidine imino proton peak estimated by reference to the G imino proton peak is consistent with the number of C·C+ pairs expected (8 to 9 C imino protons for 2 G imino protons) for the dimers displayed in the scheme shown in FIG. 2B. Sms formation was followed by NMR in the same experimental conditions ([$C_7GC_4$]=1.5 mM, pH 4.6, T=37° C.) than the gel filtration experiments described just above. The G imino proton peak is broadened out by exchange with water at 37° C. (FIG. 5C). The NMR spectra recorded as a function of the time after melting show a broadening of about 40 Hz and a reduction of the intensity of all the NMR peaks, indicating the formation of large structures with a slow tumbling rate. The initial intensity is fully restored when the sample is heated at 100° C. At equilibrium, the reduction of the spectral intensity, about 75%, is comparable to the oligonucleotide fraction found associated in sms by chromatography. However, the intensity of the NMR peaks decreases with a time constant 20 times longer than that measured by chromatography (FIG. 5D). The disproportion of the time constants measured by chromatography and NMR is merely related to the difference of the species that are taken into account by each method. The time constant derived from the chromatographic investigation is related, according to the definition given to sms, to the formation of structure whose molecular weight is larger than that of a tetramer, whereas the time constant derived from the NMR experiments reflect the formation of much longer sequences whose proton spectrum is broadened out.

Example 3

Competition Between the i-Motif Dimer and Tetramer of $C_7GC_4$(SEQ ID No: 2)

The concomitance of the evolution of the dimer and sms fractions displayed in FIG. 4 suggests that sms formation is controlled by dimer dissociation. In order to understand how the dimers and the tetramers of $C_7GC_4$ (SEQ ID No: 2) interfere with sms formation, their reduced dissociation constants were measured at different pH. The chromatograms of $C_7GC_4$ (SEQ ID No: 2) solutions recorded at different times after melting and incubation at 20° C. shows the following systematic features: the first multimer formed is always a dimer. When the oligonucleotide concentration is sufficiently high, one observes that a tetramer is formed at a slower rate. Tetramer formation is always followed by the apparition of sms. The reduced dissociation constant of the dimer, $Fi_{dimer}$, measured vs. pH from the dimer and monomer equilibrium concentrations are displayed in FIG. 7. $Fi_{dimer}$ is close to 2 $10^{-8}$ M between pH 3.5 and 5.5 and increases sharply when the solution pH is moved away from this range of values. The monomer concentration, which is controlled by the monomer-dimer equilibrium, is extremely small in the range of oligonucleotide concentrations allowing tetramer formation and for this reason the tetramer reduced dissociation constant is experimentally inaccessible. Assuming that the tetramer of $C_7GC_4$ (SEQ ID No: 2) is formed by pairing and intercalation of the seven consecutive cytidines, it was considered that its reduced dissociation constant should be comparable to that of any i-motif tetramer formed by intercalation of $C_7$ stretches and $C_7T$ was used as a model to evaluate the reduced dissociation constant of $[C_7GC_4]_4$. The chromatograms of $C_7T$ (SEQ ID No: 10) show two peaks that are eluted at the positions expected for a monomer and a tetramer. The reduced dissociation constants of $[C_7T]_4$ derived from the tetramer and monomer equilibrium concentrations are displayed vs. pH in FIG. 7. Between pH 4 and 5.5, the reduced dissociation constant, $Fi_{tetra}$, is about 200 times larger than that of the dimer. Due to the lesser sensitivity to pH of $Fi_{tetra}$, the dimer and the tetramer reduced dissociation constant are comparable around pH 6.5.

Example 4

Effect of the Temperature on the Sms Formation Time

The inventors measured by chromatography on GPC 100 column the sms formation time in 0.3 mM $C_7GC_4$ (SEQ ID No: 2) solutions, pH 4.6 vs. temperature. FIG. 8 shows that the sms half formation time varies from 0.15 hours at 55° C. to about 90 h at 20° C. with an activation energy of 143±30 kJ/M.

Example 5

Effect of the Oligonucleotide Concentration on the Sms Formation Time

FIG. 9 show that the sms half formation time decreases as the inverse of the oligonucleotide concentration. At equilibrium, the oligonucleotide fraction associated in sms increases from 13% in a 28 µM $C_7GC_4$ (SEQ ID No: 2) solution to about 80% in 0.6 mM solution at pH 4.6. The equilibrium tetramer fraction, about 10%, depends weakly on the oligonucleotide concentration. The monomer concentration is negligible in all the range of concentration explored.

Example 6

Effect of pH on the Sms Formation Time

I-motif formation involves association of neutral and protonated cytidines. For this reason, the i-motif half formation time is minimal when the product $[f_C] \times [f_{C+}]$ of the neutral and protonated cytidine fractions is maximal, i.e., when the pH is equal to the cytidine $pK_{N3}$ (Leroy, 2009). By contrast, the plot of FIG. 10 shows that the sms formation time is maximum around pH 4.4 and decreases when the pH is shifted away from this value. It is quite puzzling to note that the effect of pH on the sms formation kinetics (shorter sms formation time when the pH is shifted away from 4.4) is opposite to that observed for the i-motif formation kinetics (longer i-motif formation time when the pH is shifted away from 4.4). At equilibrium, the oligonucleotide fraction incorporated in sms is maximal around pH=4.4 and decreases when the pH is moved away from this value. The sms fractions formed at pH 4.4 depends weakly of the temperature, as shown by the similarity of the sms proportions measured at 37 and 50° C.

Example 7

The Sms Dissociation Kinetics

FIG. 11 shows the evolution vs. time of the sms fraction and of the species generated by sms dissociation. After dilution of a purified sms solution to 3 µM, the sms fraction decreases exponentially with a time constant of 0.46 h. At equilibrium the residual sms fraction is negligible. The chromatograms recorded during the first 30 minutes of the experiment show the formation of a tetramer (Te), of a species ($Te_2$) whose molecular weight is about twice that of a tetramer and of monomer. The monomer half formation time, 0.5 h., is close to the sms dissociation time. Qualitatively, this establishes that sms disruption releases short sms fragments, among which only $Te_2$ may be resolved on the GPC-100 column, and a tetramer that in turn dissociates into monomer. The similarity of the time constants for sms dissociation and monomer formation together with the exponential character of both kinetics indicate that tetramer dissociation is not limiting. At last, the chromatograms show the formation of a dimer. The initial zero slope of the plot of the dimer fraction vs. time indicates that this species is not directly generated by sms dissociation but results from monomer dimerization. The monomer and dimer equilibrium concentrations corresponds to a reduced dissociation constant $Fi=2.5 \cdot 10^{-6}$ M for the dimer at 40° C., pH 4.6 which is about one hundred times larger than that measured at 20° C. on FIG. 7.

Example 8

Effect of pH and Temperature on the Sms Dissociation Time

FIG. 12 shows that the sms lifetime is maximum around pH 4.4 and decreases at higher and lower pH. The activation energy related to sms dissociation, $E_{ac}=255\pm20$ kJ/M, seems nearly independent of pH. The sms lifetime around pH 4.4 is extraordinary long. The extrapolation of the value measured between 42 and 60° C. gives a lifetime of about 14 years at 20° C.

Example 9

Other Oligonucleotides

All the oligonucleotides of the $C_7XC_4$ (SEQ ID No: 9) family, where X is either A, T, G, or an ethane-diol spacer, as well as $C_4GC_7$ (SEQ ID No: 3), $C_4TC_7$ (SEQ ID No: 5), $C_6TC_3$ (SEQ ID No: 11), $C_7TC_3$ (SEQ ID No: 12), $C_5TC_5$ (SEQ ID No: 13), $C_5TC_2$ (SEQ ID No: 22), $C_2TC_5$ (SEQ ID No: 23) and $C_3TC_3$ (SEQ ID No: 24) associate into sms. The size of the sms, their formation and dissociation rates and the oligonucleotide fraction associated into sms at equilibrium depend on the length of the C stretches and on the nature of the non cytidine spacer. All these oligonucleotides form preferentially a dimer rather than a tetramer. The dimer may be the thermodynamically stable multimer, as this seems to be the case for $C_7GC_4$ (SEQ ID No: 2) or it may be kinetically trapped during a time exceeding experimental investigation. The inventors also observed the assembly of $C_7$ (SEQ ID No: 21) into sms as originally reported by Yamuna Kishnan and collaborators (Ghodke et al., 2007).

Oligonucleotides of 10 to 12 Nucleotides $C_4GC_7$ (SEQ ID No: 3): The half formation times of the sms of $C_7GC_4$ (SEQ ID No: 2) and $C_4GC_7$ (SEQ ID No: 3) are comparable (FIG. 8). After incubation during 68 hours at 42° C., the GPC 1000 chromatogram of a 4.4 mM $C_4GC_7$ (SEQ ID No: 3) pH 4.6 solution shows that 90% of oligonucleotides are associated in sms. The sms distribution is centered on a molecular weight corresponding to the association of 25 tetrameric units (i.e., 1200 nucleotides) and 5% of the sms include more than 90 tetrameric units (FIG. 13).

$C_7TC_4$ (SEQ ID No: 4), $C_4TC_7$ (SEQ ID No: 5) and $C_8TC_5$ (SEQ ID No: 14). The reduced dissociation constants of the dimers of $C_7TC_4$ (SEQ ID No: 4), $C_4TC_7$ (SEQ ID No: 5) and $C_8TC_5$ (SEQ ID No: 14) are at least 10 times smaller at pH 4.6 than that of $C_7GC_4$ (SEQ ID No: 2). This shows that the nature of the non-cytidine spacer contributes to the dimer stability and therefore interferes with sms formation. The chromatograms of a 1 mM $C_8TC_5$ (SEQ ID No: 14) solution pH 4.6 incubated at 42° C. during several days show that this oligonucleotide forms a stable dimer and give no indication for sms or tetramer formation. The half association times of $C_7TC_4$ (SEQ ID No: 4) and $C_4TC_7$ (SEQ ID No: 5) (FIG. 9) into sms are respectively 20 times and 3 times longer than that of $C_7GC_4$. (SEQ ID No: 2) In both cases the half association times vary as the inverse of the oligonucleotide concentration. The chromatograms recorded at 42° C. to follow sms formation in $C_4TC_7$ (SEQ ID No: 5) solutions show that the oligonucleotide fractions associated into sms are 60 and 75% in 0.3 and 3 mM solutions, respectively (FIG. 14).

$C_6TC_3$ (SEQ ID No: 11): The comparison of chromatograms recorded at 0° C. and 20° C., pH 4.6, indicates that the sms of $C_6TC_3$ are partially dissociated at 20° C. during the 4 to 6 minutes long retention time. It is noteworthy that the lifetime of $C_7GC_4$ (SEQ ID No: 2) in the same conditions is as long as years.

$C_5TC_5$ (SEQ ID No: 13): At 42° C., pH 4.6 the formation rate of $C_5TC_5$ sms is about 100 times slower than that measured for the reference $C_7GC_4$ (SEQ ID No: 2) oligonucleotide. After incubation during 5 days, in conditions close to equilibrium, the chromatogram of a 5 mM $C_5TC_5$ solution shows that the dimer, tetramer and sms fractions are 60%, 20% and 20%, respectively.

$C_7$ (SEQ ID No: 21): The association rate of $C_7$ into sms is faster than that $C_7GC_4$ (SEQ ID No: 2) but the lifetime of the sms of $C_7$ measured at different pH are 10 to 100 times shorter than those of $C_7GC_4$ (FIG. 12). This explains that oligonucleotide proportion associated in sms is smaller in $C_7$ than in $C_7GC_4$ solution.

Shorter Oligonucleotides: $C_5TC_2$ and $C_3TC_3$

As in the case of $C_7GC_4$, the association rate of $C_5TC_2$ (SEQ ID No: 22) into sms vary as the oligonucleotide concentration. However, the formation rate of the sms of $C_5TC_2$, is about 20 times slower that in the case of $C_7GC_4$. In a 2 micro molar $C_5TC_2$ solution, 50% of the oligonucleotide is associated into sms at 20° C. The sms formed in a 1 mM; solution pH 4.6; contain up to 80 tetrameric units. The lifetime of the $C_5TC_2$ sms is 7.5 hours at pH 4.6 and less that 1 minute at pH 6.

Interestingly, the association rate of $C_3TC_3$ (SEQ ID No: 24) into sms vary as the square of the oligonucleotide concentration. This observation suggests that with $C_3TC_3$, sms formation is limited by the association of the oligonucleotides into tetrameric $[C_3TC_3]_4$ building blocks, and not by the association rate of the building blocks, as for the others oligonucleotides.

Example 10

Sms Formation by Auto-Assembly of i-Motifs on a Surface

The inventors have then obtained supramolecular structures by self-association of i-motif building blocks on a surface.

A self-buffered 5 mM water solution pH 4.6 of oligonucleotide $C_7TC_4$ (SEQ ID No: 4) was incubated for 170 hours at 42° C. Green muscovite mica was freshly cleaved and treated for 3 min with 10 mM $NiCl_2$ in water. The surface was rinsed 2-times with 0.5 mM acetic acid in water and air dried. Samples were diluted 1000-fold in 0.5 mM acetic acid in water before use. 20 µl of the diluted $C_7TC_4$ solution was layered on the surface and incubated at 4° C. during 20 mM. Excess of solution was carefully removed by lateral absorption with KimWipes absorbing paper. The surface was rinsed with 30 µl of 0.5 mM acetic acid pH 4.5, air dried and observed at ambient temperature (22° C., relative humidity<32%). AFM observation was performed in air and contact mode with DNP-S and K=0.03N/m nanoprobe.

Figure 15:
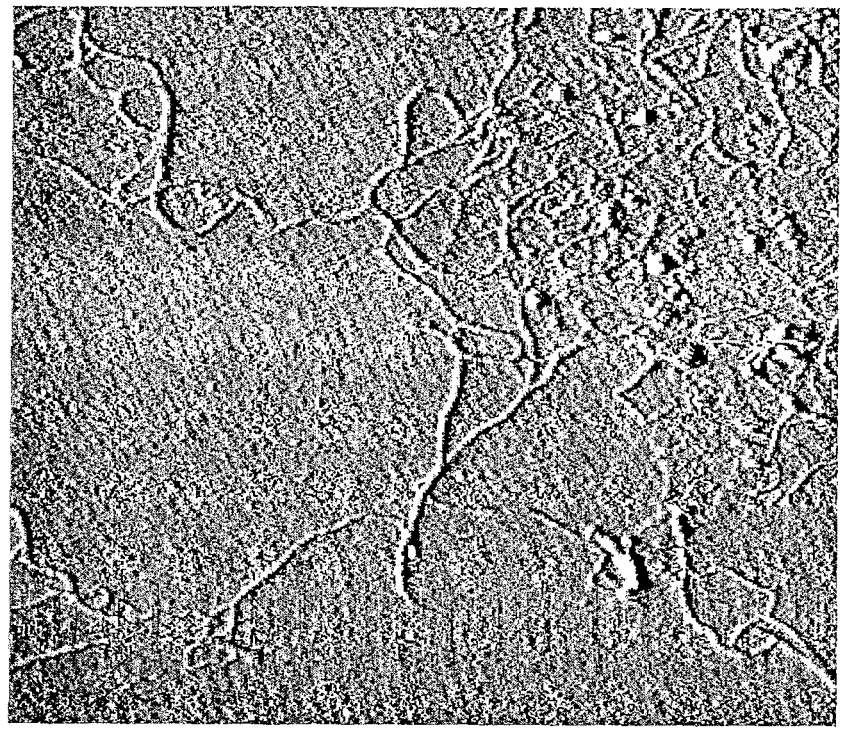
Figure 15:
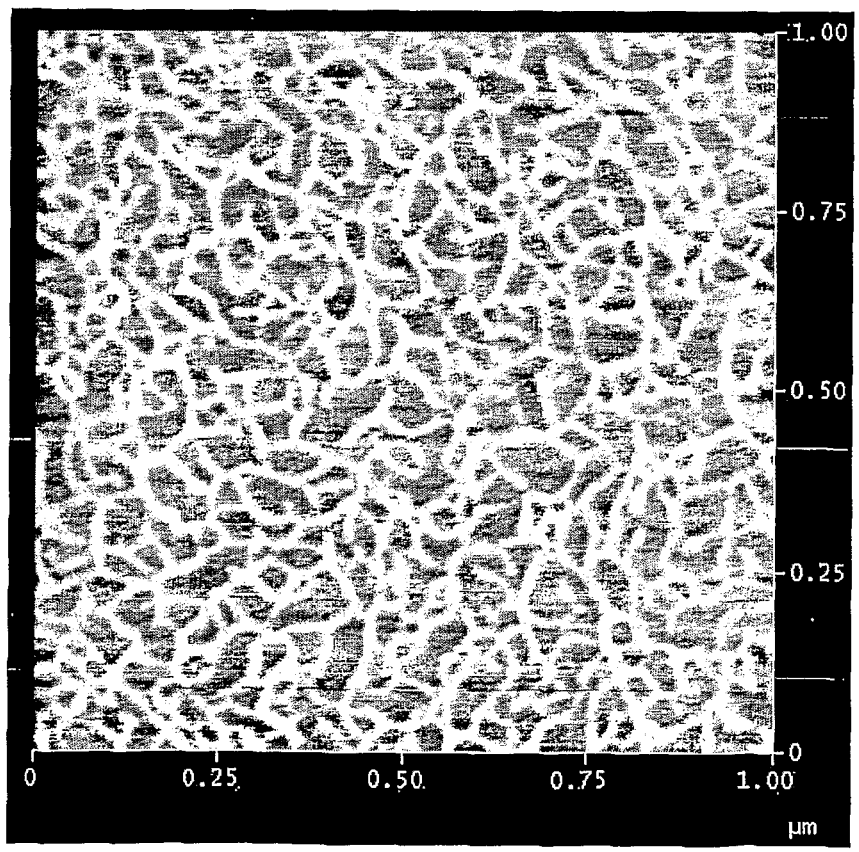

As shown in FIGS. 15 and 17, the resulting supramolecular structures constitute a 2-D network, with approximately regular 3-way nodes, the exact structure of which remains to be determined (see FIG. 16).

These networks have the following unique features:
a first is to be highly sensitive to any modulation of the surface of substrate on which self-assembly is performed. This paves the way to direct self-assembly at will by first creating on the substrate a "latent image" in which surface properties are first very slightly changed, for example by treatment with a ion or electron beam or even by an X-ray diffraction pattern. During the dynamic assembly phase, such local change can be used to modulate the affinity of building blocks which will for example preferentially accumulate on modified surfaces. At this point the rate of i-motif node formation between building blocks is predicted to have the exceptional feature to be extremely sensitive to local concentration on a highly non linear way (order of reaction is today evaluated to be at least of 3 for simple blocks), leading to block polymerization only on the "latent image trace" and offering a nice way to build structures at will.

a second is that the pH tuneability of i-motif link stability (from fraction of sec. life time to fully stable) opens the way to a very simple approach for self-repair or default removal based on sequential destabilization of a pre-established network by pH shift, followed by spontaneous exchange or relocation of damaged or incorrectly located blocks and self-ligation before final restoration of the overall network stability by a reverse pH shift.

DISCUSSION

A good knowledge of the factors that influence the sms growth is essential to control the assembly of i-motif building blocks into supramolecular structures with specific applications (Davis et al., 2002). The detail of the sms formation pathway is beyond the scope of the present data; nevertheless, some indications on the sms growing process may be derived from the experiments presented above.

i-Motif Dimer and Tetramer Stability

A constant property of $C_mXC_n$ sequences is their capacity to form stable dimers. It should be noticed that these dimers are certainly not parallel hemiprotonated duplexes. First because there is no experimental indication in the literature in favor of the existence of stable C-rich hemiprotonated duplexes in oligonucleotide solutions. In addition, these species that are considered as short-lived precursor of i-motif tetramers in fast exchange with the monomer (Canalia and Leroy, in press) should not be eluted as a dimer on gel filtration column. Two families of i-motif dimers have been described (Canalia and Leroy, 2005; Nonin et al., 1997). One is formed by the parallel arrangement of two hairpins whose loops are on the same side of the i-motif core, the other by two hairpins in a head to, tail orientation (scheme on FIG. 2B). Many conformers may coexist in each families, depending on the loop position with respect to the narrow or wide grooves, on the intercalation topology of the C·C+ pairs and on the number of cytidines in the loops. Several examples have been reported showing that dimer formation is kinetically favored by comparison with tetramer formation. At equilibrium, $T_2C_8T_2$ (SEQ ID No: 15) and $C_4TC_4$ (SEQ ID No: 16) form stable tetramers. Nevertheless, after melting and fast quenching, these oligonucleotides are eluted on gel filtration column as a dimers, and it is observed that the dimer to tetramer conversion is extremely slow (Leroy et al., 1993). The NMR study of 5mCCTCTCC (SEQ ID No: 17) (Leroy, 2003) and of 5mCCTCTCTCC (SEQ ID No: 18) (Canalia and Leroy, in press) shows that after melting these oligonucleotides are kinetically trapped into hairpin dimers and that the formation of the thermodynamically stable tetramer is extremely slow. The difference of the i-motif dimer and tetramer formation rates is certainly related to the orders of the formation reaction of each multimer. The reaction orders for dimer and tetramer formation are 2 and 3, respectively (Canalia and Leroy, 2005; Leroy, 2009). Let us suppose that dimer (D) and tetramer (Te) formation occurs via two parallel equilibriums with the monomer (M) with the rate constant indicated below:

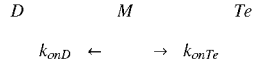
(equation 1)

Considering the formation order of each species, the initial dimer and tetramer formation rates are respectively: $k_{dimer} = k_{onD} M_0^2$ and $k_{tetra} = k_{onTe} M_0^3$ If one supposes that the rates $k_{onD}$ and $k_{onTe}$ are comparable, the initial formation rate of the tetramer should be slower than that of the dimer by a factor equal to $M_0$, the oligonucleotide concentration. It is hard to imagine that the dimer structures displayed in FIG. 2B could induce or contribute to sms formation. It is therefore tempting to regard dimer formation as a dead-end way in the sms formation pathway. The study of $C_7TC_4$ (SEQ ID No: 4) and $C_8TC_5$ (SEQ ID No: 14) give indirect arguments suggesting that the dimer stability and the sms formation rate are correlated. For instance, the slow formation rate of the sms of $C_7TC_4$ (SEQ ID No: 4) and the absence of sms in $C_8TC_5$ (SEQ ID No: 14) solution could be a consequence of the stability of the dimer formed by these oligonucleotides. It may be noticed about the stability of these dimers that the loop topology of the dimer displayed in the third scheme shown in FIG. 2B allows the formation of a cross-loop T·T pair (Leroy, 2003) which could account for the enhanced stability of the duplexes with a T spacer. If the $[C_mXC_n]_2$ dimer hinder tetramer and sms formation, it is predictable that the factors (pH, temperature, ... ) reducing the dimer stability to a greater extent than the tetramer stability should be favorable to sms formation. FIG. 10 shows that sms formation is unexpectedly accelerated when the solution pH is moved away from the cytidine $pK_{N3}$. FIG. 7, right panel shows that due to dimer dissociation, the tetramer fraction available for sms growing increases between pH 5.3 and 6.3 by more than two magnitude orders, a factor comparable to the acceleration of the sms formation rate in this range of pH.

FIG. 8 shows that the sms formation time decreases vs. temperature with a positive activation energy (255 kJ/M. for the sms of $C_7GC_4$ (SEQ ID No: 2)) whereas the i-motif tetramer formation times vary with temperature with negative activation energies ($E_{act}$=–197 and –306 kJ/M for $[TC_3]_4$ and $[TC_5]_4$, respectively (Leroy, 2009)). The lengthening of the formation time of i-motif tetramers at high temperature has previously been ascribed to the reduction of the proportion of an intermediate dimer or trimer species (Leroy, 2009). The acceleration of the sms formation time could reflect the activation energy required to dissociate the dimer that hinder sms formation.

The Sms Growing Process

By contrast with the formation time of i-motif tetramer that vary as the power of –2 of the monomer concentration, the sms formation time varies as the power of –1 (FIG. 9). This indicates that sms formation is not limited by the formation of the tetrameric i-motif building blocks (Te in FIG. 2A). This argues also against a growing process involving successive addition of monomer units to a tetramer nucleus whose rate should be strongly dependent on the oligonucleotide concentration. The i-motif of dimer of $C_7GC_4$ (SEQ ID No: 2) is more stable around pH 4.4 that the tetramer (FIG. 7). However, the extreme stability of the sms shifts the [dimer←→monomer←→tetramer←→sms] equilibriums towards sms. Considering that $k_{dimer} > k_{tetra}$ (Cf. equation 1), the dimer concentration should decrease at a rate $k=k_{ofD}*k_{tetra}/(k_{dimer}+k_{tetra})$ much slower than $k_{ofD}$. Dimer dissociation could be for this reason the limiting step of sms formation.

The pathway displayed in FIG. 2A is in part inspired by that proposed to account for the association of $C_7$ into i-wire structures (Ghodke et al., 2007). As this was observed in the formation kinetics of $[TC_n]$ (SEQ ID No: 20) tetramer (Leroy, 2009), it is likely that several $[C_7GC_4]$ (SEQ ID No: 2) tetramers differing by their intercalation topology transiently coexist. However, the species formed by intercalation of the seven consecutive cytidines of $C_7GC_4$ (Te in FIG. 2A) is expected to be the thermodynamically stable tetramer and the inventors postulate that this tetramer is the building block of the sms growing process.

Successive association by pairing and intercalation of the non-paired $C_4$ stretches of Te building blocks should results in the assembly of 2, 3, ..., n tetramers. The i-motif symmetry that gives to the assembly of several Te building blocks the same overhanging $C_4$ terminations than the building blocks themselves allows sms elongation by association of preformed $T_p$ and $T_q$ assemblies into sms including (p+q) building blocks (FIG. 2A).

The lifetime of i-motif tetramers depends strongly on the number of intercalated $C \cdot C^+$ pairs (Leroy, 2009). It is therefore predictable that the connecting i-motif blocks formed by pairing and intercalation of the $C_4$ stretches should be the weak links of sms. However, it is interesting to note that the lifetime of the sms of $C_7GC_4$, about 100 h at 40° C., pH 4.5 (FIG. 12), is about 600 times longer than that of the i-motif tetramer of $TC_4$ (SEQ ID No: 7) (Leroy, 2009). This suggests that the connecting i-motif blocks formed of the $C_4$ stretch are stabilized in the sms by staking interactions with the outer $C \cdot C^+$ pairs of the i-motif core built by the $C_7$ moiety.

The Structure of Supramolecular i-Motif Assembly

Since the sms signal disappears from the NMR spectra, NMR is obviously not appropriated to structural investigation of large sms. Nevertheless, the long sms lifetimes should allow the purification of tetramer assembly short enough to be accessible to structural investigation by NMR methods.

The formation pathway proposed just above, supposes implicitly that the sms of $C_mXC_n$ oligonucleotides are linear structures. $C \cdot C^+$ intercalation in i-motif structures requires extension of the helical rise at C—C steps up to 6.3 Å, a value almost twice that of B DNA that is close to the maximal helical stretch accessible without base-pair disruption (Lebrun and Layery, 1996). Due to its extreme helical stretch and compactness, the i-motif seems to be an unbendable structure and it may be predicted that the i-motif sms should look like extended stiff structures. Nevertheless, preliminary AFM investigations show that the structures formed are markedly influenced by the nature of the X spacer. AFM images of $C_7TC_4$ (SEQ ID No: 4) samples deposited on mica shows bent structures as long as nanometer with unexpected 120° bifurcations whereas the supramolecules of $C_7GC_4$ (SEQ ID No: 2) look like aggregated shapeless pellets (FIG. 18). Besides, as shown in Example 10, self-association of i-motifs on a surface showed that a net, rather than simple 1-D wires, is formed, demonstrating that i-motif linkers can self-associate to form three-ways nodes (FIG. 16).

To date, the exact structure of the three-ways nodes of supramolecular i-motif assemblies is not known.

Further investigations are required to give a precise description of the supra molecular structures formed by $C_mXC_n$ oligonucleotides. The structural analogy of G-rich (Burge et al., 2006; Davis and Spada, 2007; Lane et al., 2008) and i-motif multimers, the similarity of the formation pathways (Bardin and Leroy, 2008; Leroy, 2009) of i-motif tetramers and G-quadruplex are remarkable. It is also interesting to note that G-rich oligonucleotides associate also into supramolecular structures that are described as G-wire structures. &wires are also formed competitively with dimers structures. While it is assumed that i-motif sms are generated by the repetitive association of preformed tetrameric building blocks with incomplete intercalation, it is suggested that G-wire formation involves association of parallel duplexes to an out-of-register G-duplex matrix (Marsh et al., 1995).

The lifetimes of fully matched or of mismatched G-quadruplexes (Mergny et al., 2005) and i-motif structures are extremely long. For this reason, the formation kinetics of four stranded tetramers is conditioned by the slow evolution of species that are kinetically trapped (Bardin and Leroy, 2008; Leroy, 2009). It seems clear that the slow evolution of thermodynamically unstable species is also an obstacle to the formation of i-motif sms and the kinetic trapping of mismatched species is probably also a crucial limitation to G-wire elongation.

The readiness and the excellent yields of automated chemical DNA synthesis together with the availability of a large variety of artificial residues possessing functional specificities make DNA oligonucleotides an attractive building material for sms (Krishnan-Ghosh et al., 2004; Miyoshi et al., 2007; Niemeyer, 2000; Pitchiaya and Krishnan, 2006; Shen et al., 2004). In contrast with the DNA supramolecular assemblies based on Watson-Crick pairs or on G-quartets, which must be heated at melting temperature to be dissociated, the extreme sensitivity of the i-motif stability to pH allows dissociation of the i-motif sms by a mild pH change from pH 6 to about pH 7. This property could be extremely interesting in supramolecular assembly including standard DNA and i-motif sections, as well as other components such as proteins or PDNAs, by allowing a conformational switch triggered by pH.

REFERENCES

Bardin, C. and Leroy, J. L. (2008) The formation pathway of tetramolecular G-quadruplexes. *Nucleic Acids Res*, 36, 477-488.

Burge, S., Parkinson, G. N., Hazel, P., Todd, A. K. and Neidle, S. (2006) Quadruplex DNA: sequence, topology and structure. *Nucleic Acids Res*, 34, 5402-5415.

Canalia, M. and Leroy, J. L. (2005) Structure, internal motions and association-dissociation kinetics of the i-motif dimer of d(5mCCTCACTCC). *Nucleic Acids Res*, 33, 5471-5481.

Canalia, M. and Leroy, J. L. (2009) [5mCCTCTCTCC]4: an i-motif tetramer with intercalated T*T pairs. *J Am Chem Soc*, 131, 12870-12871.

Canalia, M. and Leroy, J. L. (in press) *J Amer Chem Soc*.

Cantor, C. R., Warshaw, M. M. and Shapiro, H. (1970) Oligonucleotide interactions. 3. Circular dichroism studies of the conformation of deoxyoligonucleotides. *Biopolymers*, 9, 1059-1077.

Chen, Y. and Mao, C. (2004) Putting a brake on an autonomous DNA nanomotor. *J Am Chem Soc*, 126, 8626-8627.

Davis, A. V., Yeh, R. M. and Raymond, K. N. (2002) Supramolecular assembly dynamics. *Proc Natl Acad Sci USA*, 99, 4793-4796.

Davis, J. T. and Spada, G. P. (2007) Supramolecular architectures generated by self-assembly of guanosine derivatives. *Chem Soc Rev*, 36, 296-313.

Gehring, K., Leroy, J. L. and Gueron, M. (1993) A tetrameric DNA structure with protonated cytosine.cytosine base pairs. *Nature*, 363, 561-565.

Ghodke, H. B., Krishnan, R., Vignesh, K., Kumar, G. V., Narayana, C. and Krishnan, Y. (2007) The I-tetraplex building block: rational design and controlled fabrication of robust 1D DNA scaffolds through non-Watson-Crick interactions. *Angew Chem Int Ed Engl*, 46, 2646-2649.

Guéron, M., Plateau, P. and Decorps, M. (1991) Solvent signal suppression in NMR. *Progress in nuclear magnetic resonance spectroscopy*, 23, 135-209.

Han, X., Leroy, J. L. and Gueron, M. (1998) An intramolecular i-motif: the solution structure and base-pair opening kinetics of d(5mCCT3CCT3ACCT3CC). *J Mol Biol*, 278, 949-965.

Krishnan-Ghosh, Y., Liu, D. and Balasubramanian, S. (2004) Formation of an interlocked quadruplex dimer by d(GGGT). *J Am Chem Soc*, 126, 11009-11016.

Lane, A. N., Chaires, J. B., Gray, R. D. and Trent, J. O. (2008) Stability and kinetics of G-quadruplex structures. *Nucleic Acids Res*, 36, 5482-5515.

Lebrun, A. and Layery, R. (1996) Modelling extreme stretching of DNA. *Nucleic Acids Res*, 24, 2260-2267.

Leroy, J. L. (2003) T. T pair intercalation and duplex interconversion within i-motif tetramers. *J Mol Biol*, 333, 125-139.

Leroy, J. L. (2009) The formation pathway of i-motif tetramers. *Nucleic Acids Res*, 37, 4127-4134.

Leroy, J. L., Gehring, K., Kettani, A. and Gueron, M. (1993) Acid multimers of oligodeoxycytidine strands: stoichiometry, base-pair characterization, and proton exchange properties. *Biochemistry*, 32, 6019-6031.

Marsh, T. C., Vesenka, J. and Henderson, E. (1995) A new DNA nanostructure, the G-wire, imaged by scanning probe microscopy. *Nucleic Acids Res*, 23, 696-700.

Mergny, J. L., De Cian, A., Ghelab, A., Sacca, B. and Lacroix, L. (2005) Kinetics of tetramolecular quadruplexes. *Nucleic Acids Res*, 33, 81-94.

Miyoshi, D., Karimata, H., Wang, Z. M., Koumoto, K. and Sugimoto, N. (2007) Artificial G-wire switch with 2,2'-bipyridine units responsive to divalent metal ions. *J Am Chem Soc*, 129, 5919-5925.

Niemeyer, C. M. (2000) Self-assembled nanostructures based on DNA: towards the development of nanobiotechnology. *Curr Opin Chem Biol*, 4, 609-618.

Nonin, S. and Leroy, J. L. (1996) Structure and conversion kinetics of a bi-stable DNA i-motif: broken symmetry in the [d(5mCCTCC)]4 tetramer. *J Mol Biol*, 261, 399-414.

Nonin, S., Phan, A. T. and Leroy, J. L. (1997) Solution structure and base pair opening kinetics of the i-motif dimer of d(5mCCTTTACC): a noncanonical structure with possible roles in chromosome stability. *Structure*, 5, 1231-1246.

Park, S. H., Pistol, C., Ahn, S. J., Reif, J. H., Lebeck, A. R., Dwyer, C. and LaBean, T. H. (2006) Finite-size, fully addressable DNA tile lattices formed by hierarchical assembly procedures. *Angew Chem Int Ed Engl*, 45, 735-739.

Paukstelis, P. J., Nowakowski, J., Birktoft, J. J. and Seeman, N. C. (2004) Crystal structure of a continuous three-dimensional DNA lattice. *Chem Biol*, 11, 1119-1126.

Pitchiaya, S. and Krishnan, Y. (2006) First blueprint, now bricks: DNA as construction material on the nanoscale. *Chem Soc Rev*, 35, 1111-1121.

Plateau, P. and Guéron, M. (1982) Exchangeable proton NMR without base-line distortion, using new strong-pulse sequences. *J Amer Chem Soc*, 104, 7310-7311.

Pompon, D. and Laisne, A. (2007) PDNA as building blocks for membrane-guided self-assemblies. *Biochem Soc Trans*, 35, 495-497.

Rothemund, P. W. (2006) Folding DNA to create nanoscale shapes and patterns. *Nature*, 440, 297-302.

Shen, Z., Yan, H., Wang, T. and Seeman, N. C. (2004) Paranemic crossover DNA: a generalized Holliday structure with applications in nanotechnology. *J Am Chem Soc*, 126, 1666-1674.

Yan, H., Park, S. H., Finkelstein, G., Reif, J. H. and LaBean, T. H. (2003) DNA-templated self-assembly of protein arrays and highly conductive nanowires. Science, 301, 1882-1884.

The invention claimed is:

1. A supramolecular structure comprising N $C_m$—X—$C_n$ (SEQ ID NO: 1) oligonucleotides, wherein m and n are integers between 2 and 7 and m≠n, X is selected from the group consisting of A, T, G, and a modified deoxynucleotide, N is an integer ≥8 and wherein each oligonucleotide is part of an i-motif tetramer.

2. The supramolecular structure of claim 1, wherein (m, n) is selected in the group of (4, 7) and (7, 4).

3. The supramolecular structure according to claim 1, wherein X=G.

4. The supramolecular structure according to claim 1, which comprises oligonucleotides having different sequences.

5. The supramolecular structure according to claim 4, comprising oligonucleotides of sequence $C_m$—X—$C_n$ (SEQ ID NO: 1) and terminator oligonucleotides.

6. The supramolecular structure according to claim 5, wherein at least part of said terminator oligonucleotides are covalently linked to a reactive group.

7. The supramolecular structure according to claim 1, wherein N≥50.

8. A process for producing a supramolecular structure according to claim 1, wherein said process comprises the following steps:
(i) incubating a solution of oligonucleotides of sequence $C_m$—X—$C_n$ (SEQ ID NO: 1) wherein n and m are integers between 2 and 7, m≠n, and X is selected from the group consisting of A, T, G, and a modified deoxynucleotide, in a buffer having a pH in the range 3 to 6, and
(ii) obtaining the supramolecular structure.

9. The process of claim 8, wherein the pH of said buffer is between 4 and 5.

10. The process of claim 8, wherein said incubation is performed at a temperature ranging 15° C. to 65° C.

11. The process of claim 8, wherein said oligonucleotide is between 50 μM and 1 mM.

12. The process of claim 8, wherein said buffer comprises 0.4 M NaCl, 10 mM sodium acetate and 10 mM sodium phosphate.

13. The process of claim 8, wherein said incubation is performed during at least 30 minutes.

14. The process of claim 8, wherein in step (ii), the supramolecular structure is obtained in the buffer solution.

15. The process of claim 8, wherein in step (ii), the supramolecular structure is assembled on a surface.

16. A process for dissociating at least part of a supramolecular structure as defined in claim 1, comprising a step of changing the pH of the environment of at least part of said supramolecular structure.

17. The supramolecular structure according to claim 1, wherein m and n are integers between 3 and 7.

18. A supramolecular structure comprising N $C_m$—X—$C_n$ (SEQ ID NO: 1) oligonucleotides, wherein m and n are integers between 2 and 7, X is a diol spacer, N is an integer ≥8 and wherein each oligonucleotide is part of an i-motif tetramer.

19. The supramolecular structure according to claim 18, wherein m and n are integers between 3 and 7.

20. A process for producing a supramolecular structure according to claim 18, wherein said process comprises the following steps:
(i) incubating a solution of oligonucleotides of sequence $C_m$—X—$C_n$ (SEQ ID NO: 1), wherein n and m are integers between 2 and 7 and X is a diol spacer, in a buffer having a pH in the range 3 to 6, and
(ii) obtaining the supramolecular structure.

21. The process of claim 8, wherein m and n are integers between 3 and 7.

22. The process of claim 20, wherein m and n are integers between 3 and 7.

23. The process of claim 8, wherein said incubation is performed at a temperature ranging 20° C. to 50° C.

24. The process of claim 20, wherein said incubation is performed at a temperature ranging 20° C. to 50° C.

25. The process of claim 8, wherein said incubation is performed during at least 1 hour.

26. The process of claim 20, wherein said incubation is performed during at least 1 hour.

* * * * *